(12) United States Patent
Liu et al.

(10) Patent No.: US 11,705,239 B2
(45) Date of Patent: Jul. 18, 2023

(54) METHOD AND APPARATUS FOR GENERATING IMAGE REPORTS

(71) Applicant: Alibaba Group Holding Limited, Grand Cayman (KY)

(72) Inventors: Wei Liu, Hangzhou (CN); Yu Wang, Hangzhou (CN); Chao Liu, Hangzhou (CN); Ying Chi, Hangzhou (CN); Xuansong Xie, Hangzhou (CN); Xiansheng Hua, Hangzhou (CN)

(73) Assignee: ALIBABA GROUP HOLDING LIMITED, Grand Cayman (KY)

( * ) Notice: Subject to any disclaimer, the term of this patent is extended or adjusted under 35 U.S.C. 154(b) by 468 days.

(21) Appl. No.: 16/922,131

(22) Filed: Jul. 7, 2020

(65) Prior Publication Data
US 2021/0057082 A1 Feb. 25, 2021

(30) Foreign Application Priority Data
Aug. 20, 2019 (CN) .......................... 201910769036.9

(51) Int. Cl.
*G06K 9/00* (2022.01)
*G16H 30/40* (2018.01)
*G16H 30/20* (2018.01)
*G16H 50/20* (2018.01)
*G06T 7/00* (2017.01)
*G16H 10/60* (2018.01)

(52) U.S. Cl.
CPC .......... *G16H 30/40* (2018.01); *G06T 7/0014* (2013.01); *G16H 10/60* (2018.01); *G16H 30/20* (2018.01); *G16H 50/20* (2018.01)

(58) Field of Classification Search
None
See application file for complete search history.

(56) References Cited

U.S. PATENT DOCUMENTS 8,521,561 B2 * 8/2013 Sasai ...................... G16H 15/00
705/2
9,165,117 B2 10/2015 Teller et al.
(Continued)

*Primary Examiner* — Avinash Yentrapati
(74) *Attorney, Agent, or Firm* — James J. DeCarlo; Greenberg Traurig, LLP

(57) ABSTRACT

Embodiments of the disclosure provide methods, apparatuses, and computer-readable media for generating image reports. In one embodiment, the method includes: obtaining an image to be analyzed; determining at least one reference image corresponding to the image to be analyzed, the at least one reference image corresponding to a respective reference image report; and generating, based on the reference image report, an image report corresponding to the image to be analyzed. In the method for generating an image report provided by the embodiments, by obtaining an image to be analyzed is obtained, at least one reference image corresponding to the image to be analyzed is determined; and an image report corresponding to the image to be analyzed is generated based on a respective reference image report corresponding to the at least one reference image. Therefore, medical staff are assisted in quickly writing an image report, thereby ensuring the quality and the efficiency of the image report, reducing labor costs and time costs required for collating the image report, and further improving the practicability of the method.

17 Claims, 18 Drawing Sheets

(56) References Cited

U.S. PATENT DOCUMENTS

| | | | |
|---|---|---|---|
| 10,055,543 B2* | 8/2018 | Kozuka | G06T 19/00 |
| 10,176,892 B2* | 1/2019 | Qian | G06F 16/3344 |
| 10,210,609 B2* | 2/2019 | DeVries | G06V 30/194 |
| 10,282,835 B2 | 5/2019 | Reicher et al. | |
| 10,482,606 B2 | 11/2019 | Higgins et al. | |
| 10,734,102 B2* | 8/2020 | Yakami | G16H 50/20 |
| 10,762,168 B2* | 9/2020 | Qian | G16H 15/00 |
| 10,777,307 B2* | 9/2020 | Schulze | G16H 15/00 |
| 11,289,188 B2* | 3/2022 | Mabotuwana | G16H 30/20 |
| 2003/0144886 A1* | 7/2003 | Taira | G16H 70/60 |
| | | | 705/3 |
| 2009/0192824 A1* | 7/2009 | Minakuchi | G16H 50/70 |
| | | | 705/3 |
| 2012/0176408 A1 | 7/2012 | Moriya | |
| 2012/0250961 A1* | 10/2012 | Iwasaki | G16H 15/00 |
| | | | 382/128 |
| 2013/0158368 A1 | 6/2013 | Pacione et al. | |
| 2014/0257854 A1 | 9/2014 | Becker et al. | |
| 2015/0262014 A1* | 9/2015 | Iwamura | G16H 50/20 |
| | | | 382/128 |
| 2016/0203263 A1* | 7/2016 | Maier | G16H 30/40 |
| | | | 705/2 |
| 2017/0262584 A1 | 9/2017 | Gallix et al. | |
| 2018/0166167 A1* | 6/2018 | Kanada | G06T 7/0012 |
| 2019/0131012 A1* | 5/2019 | Osawa | G06F 18/2413 |
| 2019/0139642 A1* | 5/2019 | Roberge | G06V 10/25 |
| 2020/0019617 A1* | 1/2020 | Eswaran | G06T 7/0016 |
| 2020/0027545 A1* | 1/2020 | Xie | G16B 40/00 |
| 2021/0057069 A1* | 2/2021 | Wang | G16H 15/00 |

* cited by examiner

METHOD AND APPARATUS FOR GENERATING IMAGE REPORTS

CROSS-REFERENCE TO RELATED APPLICATIONS

This application claims the benefit of priority of Chinese Application No. 201910769036.9 filed on Aug. 20, 2019, which is hereby incorporated by reference in its entirety.

BACKGROUND

Technical Field

The present application relates to the technical field of image processing, and in particular, to a method and an apparatus for generating image reports.

Description of the Related Art

Medical imaging technology refers to technology and processes for obtaining images of, inter alia, interior tissues, or certain parts of the human body in a non-invasive manner for the purpose of medical treatment or medical research. For example, the structure and density of interior tissues or an interior organ of the human body that can be displayed to medical staff in the form of an image in a certain medium (e.g., X-ray, an electromagnetic field, ultrasound, etc.) are caused by interaction with the human body. A diagnostician then performs a diagnosis based on information provided by the image so as to assess the health of a patient.

After obtaining the image information, a radiologist writes an image report based on the image information. To write an image report, the radiologist needs to review all of the images from the first to the last so as to find a key frame and, for example, a suspected lesion region therein. The radiologist then performs careful verification and manually writes an image report based on imaging findings. The above process of collating the image report, however, requires well-trained and experienced medical staff and is time-consuming and labor-intensive.

SUMMARY

Embodiments of the disclosure provide a method and an apparatus for generating image reports, which can assist medical staff in writing an image report quickly. The quality and efficiency of the image report can be guaranteed, while labor and time costs required for collating the image report are reduced.

In a first embodiment, a method is disclosed for generating an image report, the method comprising: obtaining an image to be analyzed; determining at least one reference image corresponding to the image to be analyzed, the reference image corresponding to a respective reference image report; generating, based on the reference image report, an image report corresponding to the image to be analyzed.

In a second embodiment, an apparatus for generating an image report is disclosed comprising: a first obtaining module, used to obtain an image to be analyzed; a first determination module, used to determine at least one reference image corresponding to the image to be analyzed, the reference image corresponding to a respective reference image report; and a first generation module, used to generate, based on the reference image report, an image report corresponding to the image to be analyzed.

In a third embodiment, an electronic device is disclosed comprising a memory and a processor, wherein the memory is used to store one or a plurality of computer instructions, and wherein when executed by the processor, the one or the plurality of computer instructions implement the method for generating an image report according to the first embodiment.

In a fourth embodiment, a computer storage medium used to store a computer program is disclosed wherein when executed by a computer, the computer program implements the method for generating an image report according to the first embodiment.

By obtaining an image to be analyzed, at least one reference image corresponding to the image to be analyzed is determined; and an image report corresponding to the image to be analyzed is generated based on a respective reference image report corresponding to the reference image. Therefore, medical staff are assisted in quickly writing an image report, thereby ensuring the quality and the efficiency of the image report, reducing labor costs and time costs required for collating the image report, further improving the practicability of the method, and facilitating market promotion and application.

In a fifth embodiment, a method is disclosed for generating an image report, the method comprising: obtaining an image to be analyzed; determining at least one reference image corresponding to the image to be analyzed, the reference image corresponding to a respective reference image report; obtaining an execution operation input by the user for an image report control, the image report control being used to copy the reference image report; and generating, based on the execution operation, an image report corresponding to the image to be analyzed.

In a sixth embodiment, an apparatus is disclosed for generating an image report, the apparatus comprising: a second obtaining module, used to obtain an image to be analyzed; a second determination module, used to determine at least one reference image corresponding to the image to be analyzed, the reference image corresponding to a respective reference image report, wherein the second obtaining module is further used to obtain an execution operation input by the user for an image report control, and the image report control is used to copy the reference image report; and a second generation module, used to generate, based on the execution operation, an image report corresponding to the image to be analyzed.

In a seventh embodiment, an electronic device, comprising a memory and a processor is disclosed, wherein the memory is used to store one or a plurality of computer instructions, and wherein when executed by the processor, the one or the plurality of computer instructions implement the method for generating an image report according to the fifth embodiment.

In an eighth embodiment, a computer storage medium used to store a computer program is disclosed, wherein when executed by a computer, the computer program implements the method for generating an image report according to the fifth embodiment.

In a ninth embodiment, a method for generating text is disclosed, the method comprising: obtaining an image to be analyzed; determining at least one reference image corresponding to the image to be analyzed, the reference image corresponding to respective reference text; and generating, based on the reference text, target text corresponding to the image to be analyzed.

In a tenth embodiment, an apparatus for generating text is disclosed, the apparatus comprising: a third obtaining module, used to obtain an image to be analyzed; a third determination module, used to determine at least one reference image corresponding to the image to be analyzed, the reference image corresponding to respective reference text; and a third generation module, used to generate, based on the reference text, target text corresponding to the image to be analyzed.

In an eleventh embodiment, an electronic device is disclosed, comprising a memory and a processor, wherein the memory is used to store one or a plurality of computer instructions, and wherein when executed by the processor, the one or the plurality of computer instructions implement the method for generating text according to the ninth embodiment.

In a twelfth embodiment, a computer storage medium used to store a computer program is disclosed, wherein when executed by a computer, the computer program implements the method for generating text according to the ninth embodiment.

BRIEF DESCRIPTION OF THE DRAWINGS

To describe the technical solutions in the embodiments of the present application or in the prior art more clearly, the accompanying drawings to be used for description of the embodiments or the prior art will be briefly introduced below. The accompanying drawings in the following description are some embodiments of the present application, and those of ordinary skill in the art can further obtain other accompanying drawings based on these accompanying drawings without creative efforts.

DETAILED DESCRIPTION

Figure 1A:
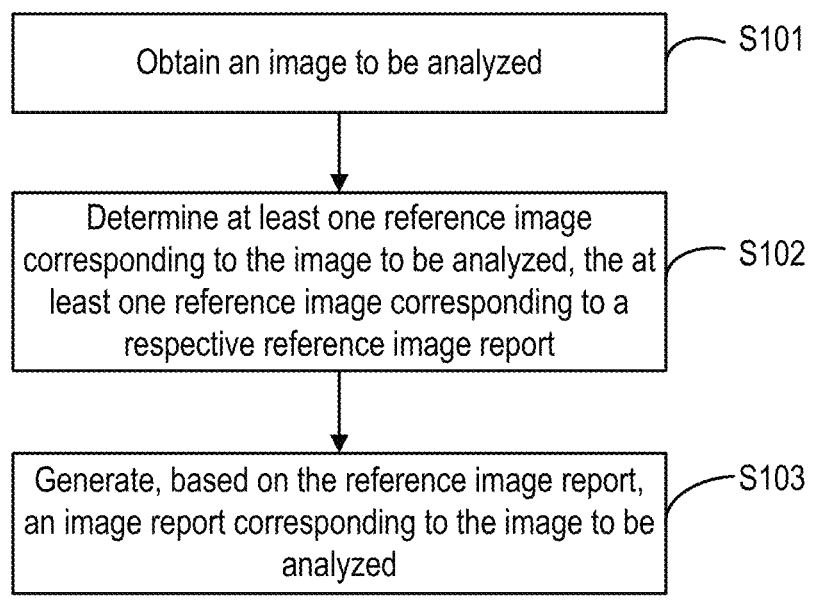
FIG. 1A is a flow diagram illustrating a method for generating an image report according to some embodiments of the disclosure.

To make the purposes, technical schemes, and advantages of the embodiments of the disclosure clearer, the technical solutions in the disclosed embodiments are described clearly and completely below with reference to the drawings of the present application. The described embodiments are merely some, rather than all of the embodiments, of the disclosure. On the basis of the embodiments in the disclosure, all other embodiments obtained by those of ordinary skill in the art without making creative efforts shall fall within the scope of the present application.

The terminology used in the embodiments of the disclosure is for the purpose of describing particular embodiments only and is not intended to limit the disclosure. The singular forms "a," "said," and "the" used in the disclosed embodiments and the appended claims are also intended to include the plural forms unless the context clearly indicates another meaning. For "a plurality of," at least two are included generally, but the case where at least one is included is not excluded.

The term "and/or" used herein is merely used for describing an association relationship of associated objects and indicates that three relationships can exist. For example, A and/or B can indicate the following three cases: A exists alone, both A and B exist, and B exists alone. In addition, the character "/" herein generally indicates that the associated objects before and after it are in an "or" relationship.

Depending on the context, the words "if" and "in case of" as used herein can be interpreted as "at the time" or "when" or "in response to the determination" or "in response to the detection." Similarly, depending on the context, the phrase "if it is determined" or "if (the stated condition or event) is detected" can be interpreted as "when it is determined" or "in response to the determination" or "when (the stated condition or event) is detected" or "in response to the detection of (the stated condition or event)."

It should also be noted that the terms "include," "comprise," or any other variation thereof are intended to encompass non-exclusive inclusions, so a commodity or system including a series of elements includes not only those elements but also other elements that are not explicitly listed, or includes elements that are inherent to this commodity or system. Without more restrictions, an element defined by the sentence "including a(n) . . ." does not exclude the existence of another identical element in the commodity or system including the element.

In addition, the order of steps of the method embodiments is provided only as an example, and is not a strict limitation. To facilitate understanding of the technical solutions of the present application, the following briefly describes current systems.

To write an image report, a radiologist needs to review each image in a series of images, in order, from the beginning image to the end image so as to find a key frame and a suspected lesion region therein. The radiologist then performs careful verification and then writes an image report based on imaging findings. However, the entire process requires well-trained and experienced medical staff, and is labor-intensive and time-consuming. Therefore, writing of an image report has often been a bottleneck in clinical diagnosis.

To improve the efficiency of writing an image report, in current systems, some tools for semi-automatically generating an image report are provided. The general implementation principle of the tools is as follows: computer vision technology is used to assist a doctor in interpreting images; all of suspected lesions are found, and types thereof are identified. Then, these findings are converted into an image report by means of natural language processing technology, and the image report is outputted. However, this method for generating an image report still has certain limitations. To develop an identification algorithm or model for all organs and all diseases, relevant costs would be extremely high, and the accuracy is not guaranteed. Currently, an automatic lesion identification model for only a single part or a single disease is developed.

Figure 1B:
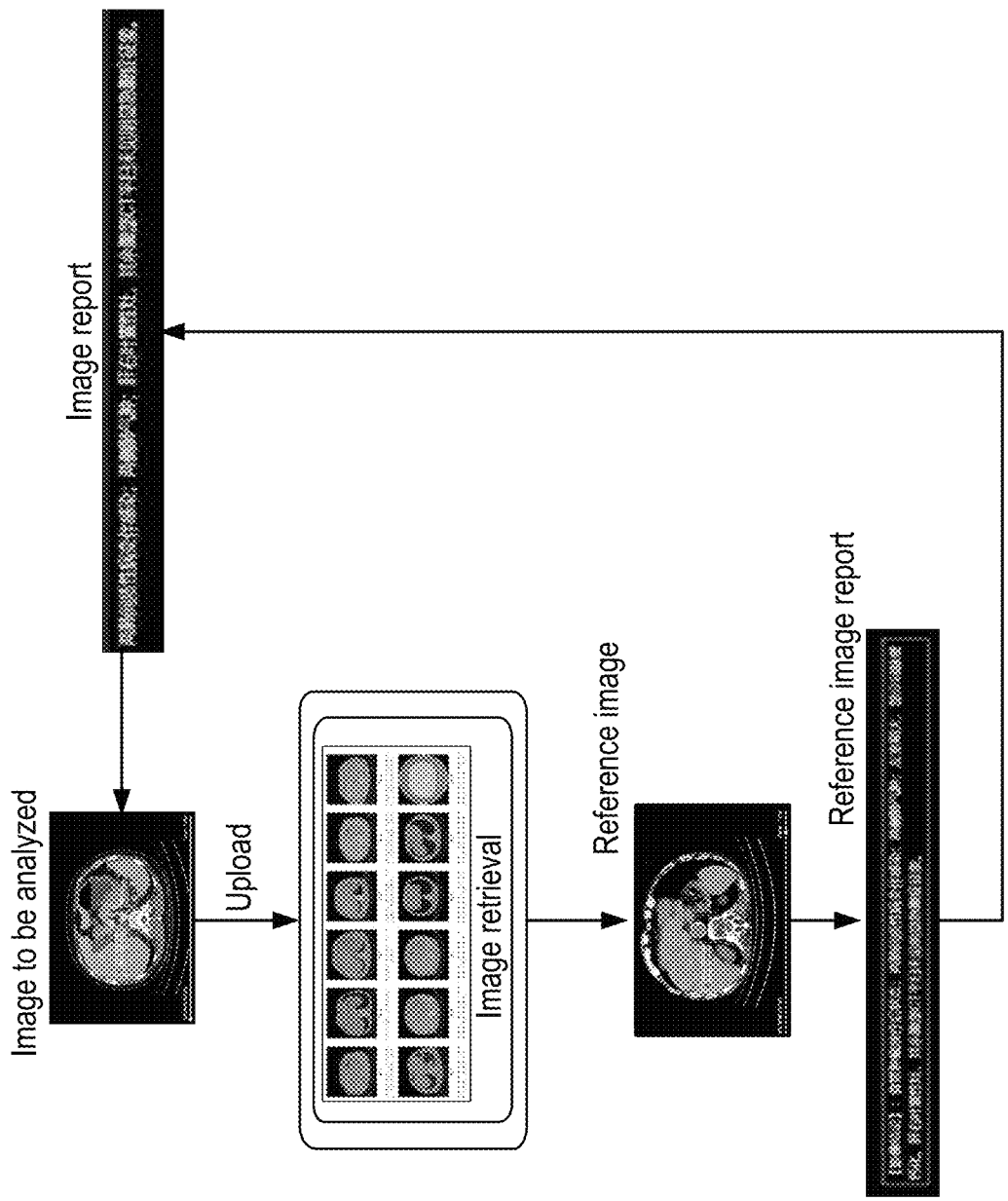
FIG. 1B is a flow diagram illustrating a method for generating an image report according to some embodiments of the disclosure.

FIG. 1A is a flow diagram illustrating a method for generating an image report according to some embodiments of the disclosure, and FIG. 1B is a flow diagram illustrating a method for generating an image report according to some embodiments of the disclosure. As shown in FIG. 1A and FIG. 1B, to eliminate the aforementioned defects in current systems, the disclosed embodiments provide methods for generating an image report. These methods may be executed by an apparatus for generating an image report. Such an apparatus may be implemented as software or a combination of software and hardware. Specifically, the method for generating an image report may include the following steps.

Step S101: obtain an image to be analyzed. In the illustrated embodiment, the image comprises a digital image or similar computer-displayable image or image file.

The image to be analyzed includes image information that needs to be recorded in an image report. The image to be analyzed may be an image such as, but not limited to, an X-ray image, an ultrasound image, a computed tomography (CT) image, a Magnetic Resonance Imaging (MRI) image, etc. In addition, this embodiment does not limit a specific method for obtaining an image to be analyzed. For example, the image to be analyzed may be directly uploaded by a user to a generation apparatus, so the generation apparatus can directly obtain the image to be analyzed. Alternatively, after an image to be analyzed is captured using an imaging apparatus, the imaging apparatus can be communicatively connected to the generation apparatus. The imaging apparatus can then transmit the captured image to the generation apparatus, so the generation apparatus obtains the image to be analyzed. Those skilled in the art may utilize other techniques to providing an image to be analyzed, as long as an image to be analyzed can be obtained, and the disclosure does not limit the ways in which an image to be analyzed may be generated.

Step S102: determine at least one reference image corresponding to the image to be analyzed, the reference image corresponding to a respective reference image report.

The reference image may be at least one of a plurality of pre-configured historical images having reference image reports. The reference image report is report information corresponding to the reference image and meeting a pre-configured standard. The pre-configured standard may be a rule generated based on medical specifications and medical advice, and the pre-configured standard is used to evaluate report information. In some scenarios with different medical specifications and/or medical advice, the pre-configured standard may be different depending on the specific scenario. The reference image report can achieve the following: anyone obtaining a reference image report corresponding to a reference image can clearly and intuitively learn about medical information included in the reference image, such as whether a lesion exists, a lesion type, a lesion size, a lesion position, a lesion period, etc.

In addition, the reference image report may a structured image report, a semi-structured image report, or an unstructured image report. Specifically, the structured image report may include structured data. The structured data may refer to data logically represented and implemented by, for example, a two-dimensional table structure. The semi-structured image report may include semi-structured data. In some embodiments, the semi-structured data may not be compatible with the data model structure of a relational database or the data model structure formed by associating data tables in other forms. However, the semi-structured data may include a relevant flag, and the relevant flag is used to separate semantic elements and layer records and fields. The unstructured image report may include unstructured data. The unstructured data refers to data having an irregular or incomplete data structure, having no predefined data model, and/or difficult to be represented by a two-dimensional logical table in a database. For example, the unstructured data may be a document of any format, text, an image, an HTML, a report form of any type, image and audio/video information, etc.

Specifically, as shown in FIG. 1B, after the image to be analyzed is obtained, analysis and recognition may be performed on the image to be analyzed. That is, image retrieval is performed using a pre-configured database based on the image to be analyzed, so at least one reference image can be determined based on a recognition result. In some embodiments, the image retrieval is performed by issuing a query to the pre-configured database using the image. The number of determined reference images may be one or more. For example, the at least one reference image may include a reference image 1, a reference image 2, and a reference image 3. In addition, each determined reference image corresponds to a respective reference image report. For example, the reference image 1 corresponds to a reference image report 1; the reference image 2 corresponds to a reference image report 2; the reference image 3 corresponds to a reference image report 3. Regarding the determining at least one reference image, this embodiment is not limited to a specific implementation, and those skilled in the art may use alternative configurations based on a specific application scenario. For example, a plurality of pre-stored historical images may be obtained, and at least one reference image is determined by determining the similarity between the historical image and the image to be analyzed. That is, if the similarity between the historical image and the image to be analyzed is greater than or equal to a pre-configured threshold, then the historical image is determined to be a reference image.

Step S103: generate, based on the reference image report, an image report corresponding to the image to be analyzed.

After the reference image report is obtained, an image report corresponding to the image to be analyzed may be generated based on the reference image report. As shown in FIG. 1B, an image report corresponding to the image to be analyzed may be generated based on the respective reference image report corresponding to the reference image. Specifically, this embodiment does not limit a specific method for generating an image report, and those skilled in the art may configure the generation of an image report based on a specific application scenario and application requirements. For example, the reference image report may be directly determined to be an image report corresponding to the image to be analyzed. Alternatively, a report template or report frame data in the reference image report may also be obtained. Then, an image parameter in the image is obtained, and an image report corresponding to the image to be analyzed is generated based on the image parameter and the report template/report frame data.

It should be noted that the image to be analyzed in this embodiment may refer to a medical image, a photo or video data obtained by means of a camera apparatus, etc. In the following example, a photo is used as an image to be analyzed for description. In an applicable scenario, a user may take travel photos during travels, and the travel photos may include landscape images, building images, etc., so a plurality of images to be analyzed can be obtained. To record impressions and memorable moments, the user may often write a travelogue in combination with the travel photos. In this case, to facilitate writing and collation of the travelogue, the user may obtain, for the travel photo, at least one reference travel photo (a reference image) corresponding to the travel photo (an image to be analyzed) in a pre-configured database. A plurality of pre-configured reference travel photos and reference travelogue information corresponding to the reference travel photos are stored in the database. Specifically, obtaining at least one reference travel photo corresponding to the travel photo may comprise determining at least one reference travel photo based on landscape information and building information in the travel photo. After the reference travel photo is obtained, travelogue information corresponding to the travel photo may be generated based on the reference travelogue information corresponding to the reference travel photo. After the travelogue information is obtained, the user may further selectively adjust or modify the travelogue information based on requirements. Therefore, travelogue information meeting personalized requirements of the user can be obtained, and the quality and the efficiency of writing and collating, by the user, the travelogue information are improved.

In the method for generating an image report provided by this embodiment, by obtaining an image to be analyzed, at least one reference image corresponding to the image to be analyzed is determined; and an image report corresponding to the image to be analyzed is generated based on a respective reference image report corresponding to the reference image. As a result, medical staff are assisted in quickly writing an image report, thereby ensuring the quality and the efficiency of the image report, reducing labor costs and time costs required for collating the image report, further improving the practicability of the method, and facilitating promotion and application.

Figure 2:
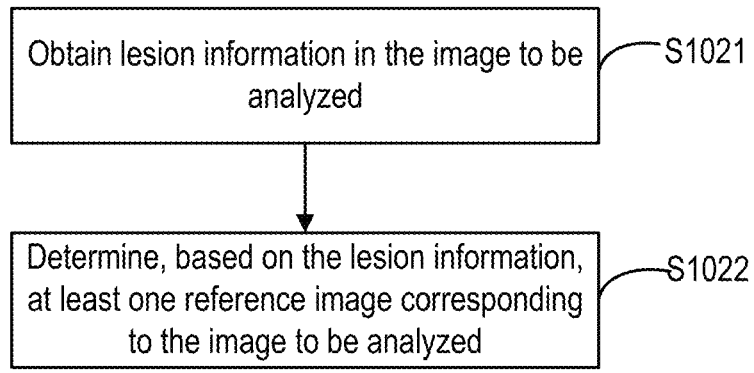
FIG. 2 is a flow diagram illustrating a method for determining at least one reference image corresponding to the image to be analyzed according to some embodiments of the disclosure.
Figure 3:
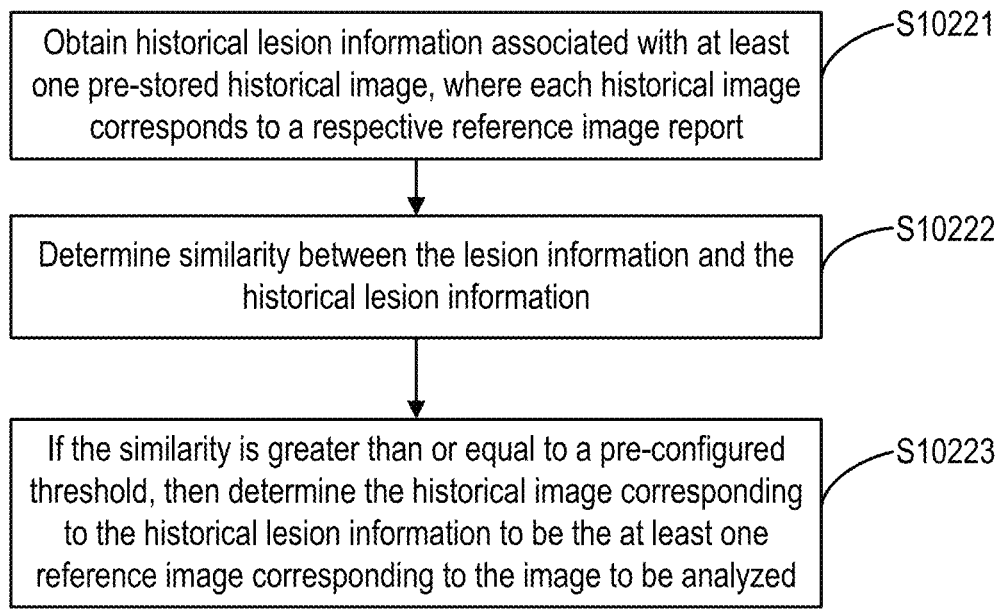
FIG. 3 is a flow diagram illustrating a method for determining, based on the lesion information, at least one reference image corresponding to the image to be analyzed according to some embodiments of the disclosure.

FIG. 2 is a flow diagram illustrating a method for determining at least one reference image corresponding to an image to be analyzed according to some embodiments of the disclosure. FIG. 3 is a flow diagram illustrating a method for determining, based on lesion information, at least one reference image corresponding to an image to be analyzed according to some embodiments of the disclosure. Based on the aforementioned embodiments, the following description is provided with reference to FIGS. 2 and 3. This embodiment does not limit a specific method for determining at least one reference image corresponding to an image to be analyzed, and those skilled in the art can adjust the embodiments based on specific application requirements. In the illustrated embodiment, determining at least one reference image corresponding to an image to be analyzed in this embodiment may include the following steps.

Step S1021: obtain lesion information in an image to be analyzed.

In the illustrated embodiment, the lesion information includes one or more of the following: a lesion type, a lesion size, a lesion shape, a lesion position, and a lesion period. Alternatively, the lesion information may not be limited to the aforementioned information, and may also include other information such as a lesion damage degree, a lesion change trend, etc.

In addition, the illustrated embodiment does not limit a specific method for obtaining lesion information. For example, the lesion information in the image to be analyzed may be identified by means of pre-configured image detection technology. Alternatively, tagging operation performed by the user on the lesion information in the image to be analyzed may also be obtained, and the lesion information is determined based on the tagging operation. Those skilled in the art may use alternative configurations based on specific application requirements as long as lesion information in an image to be analyzed can be accurately obtained, which will not be described herein again.

Step S1022: determine, based on the lesion information, at least one reference image corresponding to the image to be analyzed.

After the lesion information is obtained, analysis and processing may be performed on the lesion information, and at least one reference image corresponding to the image to be analyzed may be determined based on an analysis and processing result. Specifically, as shown in FIG. 3, the determining, based on the lesion information, at least one reference image corresponding to the image to be analyzed may include the following steps.

Step S10221: obtain historical lesion information associated with at least one pre-stored historical image, where each historical image corresponds to a respective reference image report.

The historical image is pre-stored image information having been tagged with historical lesion information, and each historical image corresponds to a respective reference image report. It should be noted that regarding the historical lesion information, in one embodiment, the historical lesion information may be a lesion result manually tagged by medical staff. In another embodiment, the historical lesion information is a result obtained by means of identification performed using a pre-configured lesion identification algorithm.

Further, the at least one historical image may include image information of different parts, different types, and different data modalities. To improve the efficiency of generating an image report, after the image to be analyzed is obtained, an image part, an image type, or a data modality of the image to be analyzed may be firstly obtained. Next, an analysis and comparison are performed on at least one historical image and the image to be analyzed, where the at least one historical image and the image to be analyzed are of the same image part, image type, or data modality. For example, the plurality of existing historical images includes a lung image set, a head image set, or an abdomen image set. If the image to be analyzed is a head image, then, analysis and comparison are firstly performed on the head image set and the image to be analyzed so as to improve the accuracy and the efficiency of determining a reference image.

Step S10222: determine similarity between the lesion information and the historical lesion information.

After the historical lesion information in the at least one historical image is obtained, analysis and comparison may be performed on the lesion information and the historical lesion information in the at least one historical image. Specifically, a comparison may be performed with respect to at least one of a lesion type, a lesion size, a lesion shape, a lesion position, or a lesion period, so the similarity between the lesion information and the historical lesion information can be obtained. To improve the accuracy and the reliability of determining a reference image, if the lesion information and the historical lesion information meet a similarity condition, then it can be determined that all of the manifestations in the lesion information are similar to all of the manifestations in the historical lesion information.

Step S10223: if the similarity is greater than or equal to a pre-configured threshold, then determine the historical image corresponding to the historical lesion information to be the at least one reference image corresponding to the image to be analyzed.

In one embodiment, the pre-configured threshold is a pre-configured similarity threshold. The similarity threshold is a minimal standard for determining a reference image. This embodiment does not limit a specific value range of the pre-configured threshold, and those skilled in the art may use alternative configurations based on specific application requirements. For example, the pre-configured threshold may be 90%, 95%, 98%, 98.5%, etc. If the similarity is greater than or equal to the pre-configured threshold, then it is indicated that the historical lesion information is similar to the lesion information in the image to be analyzed. In this case, a report of the historical image corresponding to the historical lesion information can be used to assist in generating an image report corresponding to the image to be analyzed. Therefore, the historical image corresponding to the historical lesion information can be determined to be the at least one reference image.

In some embodiments, if the similarity is greater than or equal to the pre-configured threshold, then the determined at least one reference image may include two types of historical images. The historical lesion information of one of the two types of historical images is exactly the same as the lesion information in the image to be analyzed, and the historical lesion information of the other one of the two types of historical images is not exactly the same as the lesion information in the image to be analyzed. However, the aforementioned historical images of different types may have different determination thresholds. Therefore, to further improve the accuracy of determining a historical image, the pre-configured threshold may include a first threshold and a second threshold, and the first threshold is greater than the second threshold. Correspondingly, the determining the historical image corresponding to the historical lesion information to be the at least one reference image corresponding to the image to be analyzed may include the following steps S102231 and S102232.

Step S102231: if the similarity is greater than or equal to the first threshold, then determine the historical image corresponding to the historical lesion information to be at least one first reference image corresponding to the image to be analyzed.

In one embodiment, the first threshold is a pre-configured similarity threshold. The similarity threshold is a minimal standard for determining a first reference image. The first reference image is a historical image substantially the same as the image to be analyzed. In specific applications, this embodiment does not limit a specific value range of the first threshold, and those skilled in the art may use alternative configurations based on specific application requirements. For example, the first threshold may be 98%, 98.5%, 99%, 99.5%, etc. If the similarity is greater than or equal to the first threshold, then it is indicated that the historical lesion information is substantially the same as the lesion information in the image to be analyzed. In this case, a report of the historical image corresponding to the historical lesion information can be virtually determined to be an image report corresponding to the image to be analyzed. Therefore, the historical image corresponding to the historical lesion information can be determined to be the first reference image.

Step S102232: if the similarity is less than the first threshold and is greater than or equal to the second threshold, then determine the historical image corresponding to the historical lesion information to be at least one second reference image corresponding to the image to be analyzed.

In one embodiment, the second threshold is a pre-configured similarity threshold. The similarity threshold is a minimal standard for determining a second reference image. The second reference image is a historical image highly similar to the image to be analyzed. In specific applications, this embodiment does not limit a specific value range of the second threshold, and those skilled in the art may use alternative configurations based on specific application requirements as long as the second threshold is less than the first threshold. For example, the second threshold may be 95%, 96.5%, 97%, 97.5%, etc. If the similarity is less than the first threshold and is greater than or equal to the second threshold, then it is indicated that the historical lesion information is highly similar to the lesion information in the image to be analyzed. In this case, a report of the historical image corresponding to the historical lesion information can be used to assist in generating an image report corresponding to the image to be analyzed. Therefore, the historical image corresponding to the historical lesion information can be determined to be the second reference image.

In some embodiments, in addition to determining a reference image by determining similarity of lesion information, the determining at least one reference image corresponding to the image to be analyzed may also be performed in another manner, that is, a reference image is determined by determining image similarity. Specifically, at least one pre-stored historical image is directly obtained, and similarity between the image to be analyzed and the historical image is determined. If the similarity is greater than or equal to a pre-configured similarity threshold, then the historical image corresponding to the similarity may be determined to be the reference image. Similarly, the number of determined reference images may be one or more.

It is conceivable that to further improve the practicality of the method, after the determining at least one reference image corresponding to the image to be analyzed, the method in this embodiment may further include the following step S201.

Step S201: display, in descending order of the similarity, the at least one reference image and the respective reference image report corresponding to the at least one reference image.

The similarity may refer to the similarity between the lesion information and the historical lesion information in the reference image, and different reference images correspond to different similarity. In general, the degree of similarity can reflect a reference degree of the respective reference image report corresponding to the at least one reference image, and higher similarity indicates a higher reference degree corresponding to a reference image report. Therefore, to improve the efficiency of generating an image report, after the at least one reference image is obtained, the reference image and the respective reference image report corresponding to the at least one reference image are displayed in descending order of the similarity, so the user can quickly obtain a reference image report having relatively high similarity, thereby ensuring the quality and the efficiency of generating an image report.

In this embodiment, lesion information in an image to be analyzed is obtained, and at least one reference image corresponding to the image to be analyzed is determined based on the lesion information, thereby effectively ensuring the accuracy and the reliability of determining a reference image, ensuring the efficiency of determining a reference image, and further improving the quality and the efficiency of generating an image report.

Figure 4:
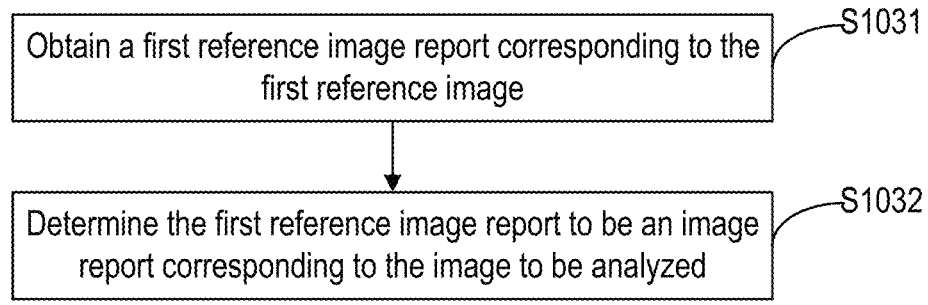
FIG. 4 is a flow diagram illustrating a method for generating, based on the reference image report, an image report corresponding to the image to be analyzed according to some embodiments of the disclosure.

FIG. 4 is a flow diagram illustrating a method for generating, based on a reference image report, an image report corresponding to an image to be analyzed according to some embodiments of the disclosure. Based on the aforementioned embodiments, the following description is provided with reference to FIG. 4. If obtained reference images include a first reference image, then the generating, based on a reference image report, an image report corresponding to an image to be analyzed in this embodiment may include the following steps.

Step S1031: obtain a first reference image report corresponding to the first reference image.

The first reference image is a historical image substantially the same as the image to be analyzed. After the first reference image is obtained, the first reference image report corresponding to the first reference image may be obtained using a mapping relationship between the first reference image and the first reference image report. The first reference image report may be a structured data report, a semi-structured data report, or an unstructured data report.

Step S1032: determine the first reference image report to be an image report corresponding to the image to be analyzed.

Because the first reference image is a historical image substantially the same as the image to be analyzed, after the first reference image report is obtained, the first reference image report may be directly determined to be an image report corresponding to the image to be analyzed, thereby effectively improving the quality and the efficiency of generating an image report corresponding to the image to be analyzed.

Figure 5:
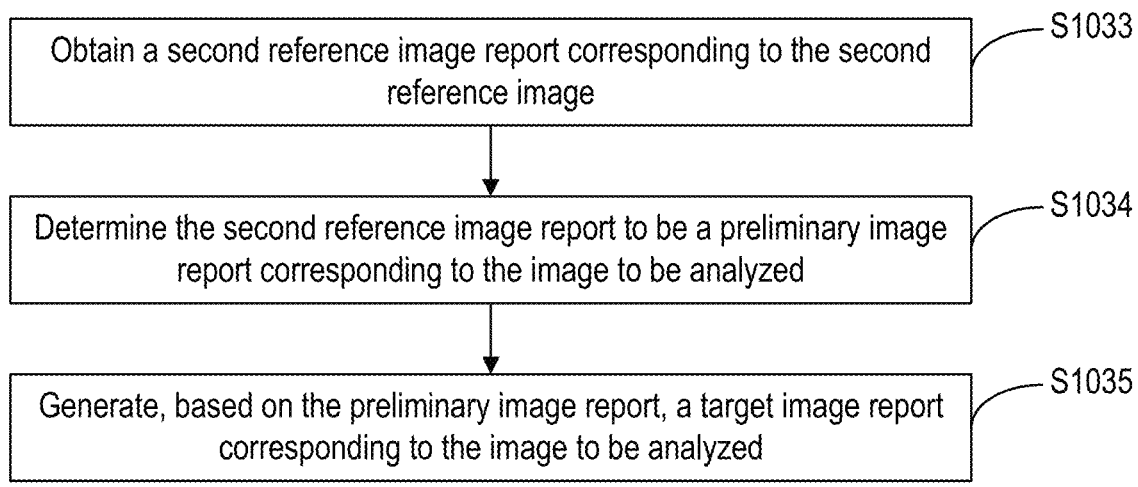
FIG. 5 is a flow diagram illustrating a method for generating, based on the reference image report, an image report corresponding to the image to be analyzed according to some embodiments of the disclosure.
Figure 6:
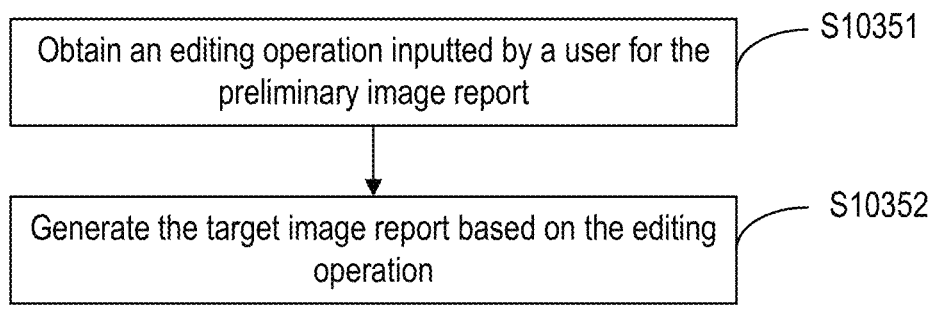
FIG. 6 is a flow diagram illustrating a method for generating, based on the preliminary image report, a target image report corresponding to the image to be analyzed according to some embodiments of the disclosure.

FIG. 5 is a flow diagram illustrating a method for generating, based on a reference image report, an image report corresponding to an image to be analyzed according to some embodiments of the disclosure. FIG. 6 is a flow diagram illustrating a method for generating, based on a preliminary image report, a target image report corresponding to an image to be analyzed according to some embodiments of the disclosure. Based on the aforementioned embodiments, the following description is provided with reference to FIGS. 5 and 6. If obtained reference images include a second reference image, then the generating, based on a reference image report, an image report corresponding to an image to be analyzed in this embodiment may include the following steps.

Step S1033: obtain a second reference image report corresponding to a second reference image.

The second reference image is a historical image highly similar to the image to be analyzed. After the second reference image is obtained, the second reference image report corresponding to the second reference image may be obtained using a mapping relationship between the second reference image and the second reference image report. The second reference image report may be a structured data report, a semi-structured data report, or an unstructured data report.

Step S1034: determine the second reference image report to be a preliminary image report corresponding to the image to be analyzed.

Step S1035: generate, based on the preliminary image report, a target image report corresponding to the image to be analyzed.

The second reference image is a historical image highly similar to the image to be analyzed. However, relatively high similarity indicates that a difference still exists between the second reference image and the image to be analyzed. Therefore, the second reference image report cannot be directly used as an image report corresponding to the image to be analyzed. To improve the accuracy and the efficiency of generating an image report corresponding to the image to be analyzed, the second reference image report may firstly be determined to be the preliminary image report corresponding to the image to be analyzed so as to reuse a large amount of content in the second reference image report, and then the preliminary image report is adjusted based on the difference between the image to be analyzed and the second reference image, so a target image report corresponding to the image to be analyzed can be obtained.

Specifically, as shown in FIG. 6, one embodiment is as follows: the generating, based on the preliminary image report, a target image report corresponding to the image to be analyzed in this embodiment may include the following steps.

Step S10351: obtain an editing operation input by the user for the preliminary image report.

Step S10352: generate the target image report based on the editing operation.

After the preliminary image report is obtained, the user may perform editing operations on content in the preliminary image report. The editing operation may include at least one of an addition operation, deletion operation, modification operation, etc. Specifically, the user may adjust content in the preliminary image report differently in the description from that of the image to be analyzed, so a target image report can be obtained. The target image report accurately and effectively describes medical information included in the image to be analyzed.

In actual applications, a reference image exactly the same as an image to be analyzed may not be found. Therefore, generally, certain differences exist between an obtained reference image and the image to be analyzed. Some of the differences do not affect the generation of an image report, but the others may affect the generation of the image report.

Therefore, to improve the quality and the accuracy of generating a target image report, after the determining at least one reference image corresponding to the image to be analyzed, the method in this embodiment may further include the following steps S104 and S105.

Step S104: obtain differential information between the reference image and the image to be analyzed, the differential information, including a differential region and a differential degree corresponding to the differential region.

Step S105: if the differential degree is greater than or equal to a pre-configured difference threshold, then distinctively display the differential region in the reference image.

Specifically, after the at least one reference image is obtained, analysis and comparison may be performed on the reference image and the image to be analyzed, so the differential information between the reference image and the image to be analyzed can be obtained. The differential information may include a differential region and a differential degree corresponding to the differential region. If the differential degree is greater than or equal to the pre-configured difference threshold, then it is indicated that the difference between the reference image and the image to be analyzed is relatively large. To enable the user to learn whether the differential region affects the image report, a differential region having a relatively large difference may be distinctively displayed. For example, the differential region may be displayed in a highlighted manner, tags in different colors may be used in distinctively displaying the differential region, etc.

For example, the differential information between the reference image and the image to be analyzed includes a first differential region, a second differential region, and a third differential region and a first differential degree, a second differential degree, and a third differential degree corresponding to the differential regions. The second differential degree is greater than the first differential degree, and the first differential degree is greater than the third differential degree. In this case, each of the differential degrees may be compared with the pre-configured difference threshold. If the second differential degree is greater than the pre-configured difference threshold, and if both the first differential degree and the third differential degree are less than the pre-configured difference threshold, then the second differential region in the reference image is displayed in a highlighted manner. It is conceivable that the position of the second differential region in the image to be analyzed corresponds to the position of the second differential region in the reference image. The second differential region is displayed in a highlighted manner, so the user can determine whether the second differential region affects the content of the image report, thereby further ensuring the quality and the efficiency of generating an effect report.

Further, in another embodiment, automatically generating, by a generation apparatus based on a preliminary image report, a target image report corresponding to an image to be analyzed includes the following steps.

Step S10353: obtain differential information between an image to be analyzed and a second reference image.

Step S10354: adjust a preliminary image report based on the differential information so as to obtain a target image report.

The differential information may include different information about any one of a lesion position, a lesion size, a lesion shape, a lesion type, a lesion period, etc. After the differential information is obtained, description information in the preliminary image report corresponding to the differential information may be locked based on the differential information, and then the description information can be automatically adjusted based on the differential information, so a target image report can be obtained.

It should be understood that to ensure the accuracy and the reliability of generating a target image report, after the target image report is obtained, the target image report may be manually approved. The target image report can be stored or applied only after the target image report is successfully approved. If the target image report fails to be approved, then the target image report may be tagged, so relevant staff can adjust and update the target image report in a timely manner. Therefore, the accuracy of description in the target image report is effectively ensured, and the accuracy of the method is further improved.

Further, after the determining at least one reference image corresponding to the image to be analyzed, the method in this embodiment may further include the following steps S106 and S107.

Step S106: obtain a keyword input by the user for the image to be analyzed.

Step S107: perform, based on the keyword, relevancy ranking on the at least one reference image.

In specific applications, when determining at least one reference image corresponding to the image to be analyzed, the user may input a keyword for the image to be analyzed. The keyword may be an image keyword corresponding to the image to be analyzed or a report keyword corresponding to the image report of the image to be analyzed. Relevancy ranking may be performed on the determined at least one reference image based on the obtained keyword.

For example, when generating an image report for an image to be analyzed, the user may input both the image to be analyzed and an image keyword. After determining at least one reference image corresponding to the image to be analyzed, the inputted image keyword may be used to perform relevancy ranking on the determined at least one reference image. Alternatively, when generating an image report for an image to be analyzed, the user may input both the image to be analyzed and a report keyword. After determining at least one reference image corresponding to the image to be analyzed, a respective reference image report corresponding to each reference image may be obtained. Then, the relevancy between the report keyword and the reference image report is obtained and ranking is performed on the determined at least one reference image based on the relevancy corresponding to the respective reference image report, so the user can easily find a reference image report closest to the image to be analyzed.

In some embodiments, the user may also search for all of image data relevant to the image report. For example, the user may input an image report keyword, search a database for all of image reports relevant to the image report keyword, determine image data corresponding to the image reports, and display the image data. In this embodiment, all of image data relevant to certain report data can be found and the image data can be ranked and displayed based on relevancy, thereby effectively meeting requirements of the user for searching for image data based on a keyword.

Figure 7:
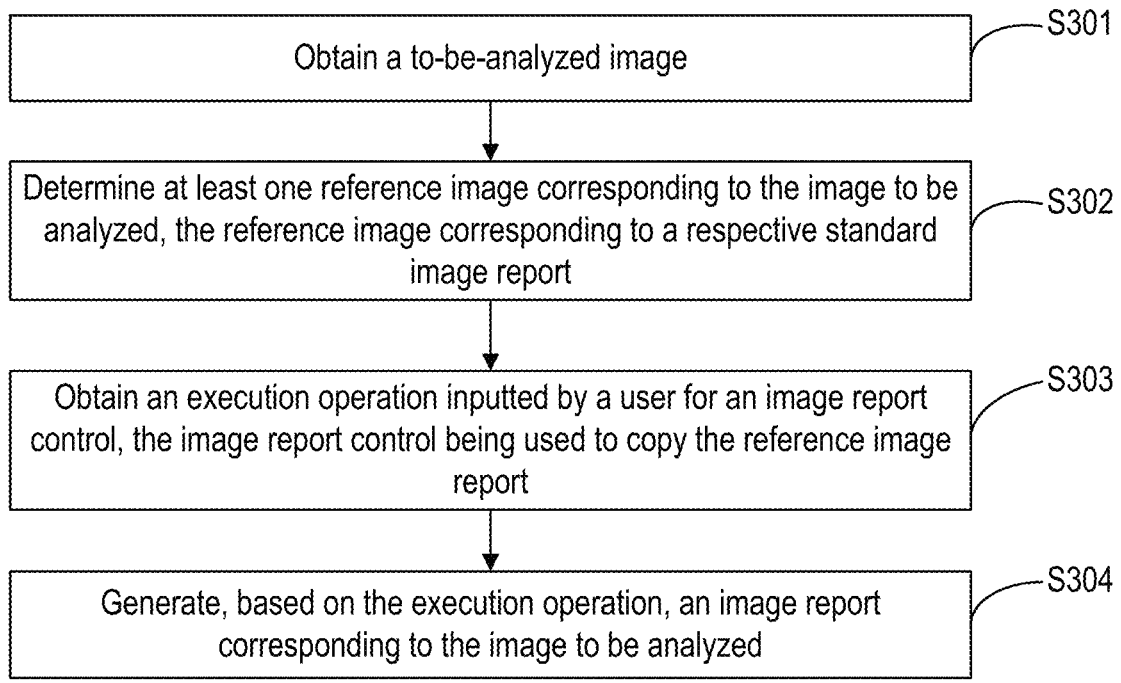
FIG. 7 is a flow diagram illustrating a method for generating an image report according to some embodiments of the disclosure.

FIG. 7 is a flow diagram illustrating a method for generating an image report according to some embodiments of the disclosure. As shown in FIG. 7, this embodiment provides another method for generating an image report. This generation method is executed by an apparatus for generating an image report. The generation apparatus may be implemented as software or a combination of software and hardware. Specifically, the method for generating an image report may include the following steps.

Step S301: obtain an image to be analyzed.

Step S302: determine at least one reference image corresponding to the image to be analyzed, the reference image corresponding to a respective reference image report.

In some embodiments, steps S301 and S302 are similar to steps S101 and S102 described previously. For details of these steps, please refer to the description in the aforementioned embodiment; the details will not be described herein again.

Step S303: obtain an execution operation input by the user for an image report control, the image report control being used to copy the reference image report.

Step S304: generate, based on the execution operation, an image report corresponding to the image to be analyzed.

The image report control is a pre-configured application control used to copy the reference image report. For example, the image report control may be a one-click copy control or a drag-and-drop copy control. The image report control may copy the reference image report in whole or in part. After the reference image report is obtained, the user may input an execution operation for the image report control. After the execution operation input by the user for the image report control is received, the reference image report can be copied. After the reference image report is copied, an image report corresponding to the image to be analyzed may be generated based on the reference image report having been subjected to the copy operation. Step 304 may be performed similar to that of step S104 in the aforementioned embodiment. For details, please refer to the foregoing description, the details will not be described herein again.

In the illustrated embodiment, the method may also include the methods in the aforementioned embodiments shown in FIG. 2 through FIG. 6. For the parts not described in detail in this embodiment, please refer to the related description of the embodiments shown in FIG. 2 through FIG. 6. For the execution process and the technical effect of the technical solution, please refer to the description in the embodiments shown in FIG. 2 through FIG. 6, and details will not be described herein again.

In the method for generating an image report provided by this embodiment, by obtaining an image to be analyzed, at least one reference image corresponding to the image to be analyzed is determined; and then an execution operation input by the user for an image report control is obtained, so an image report corresponding to the image to be analyzed can be generated based on the execution operation. Therefore, medical staff are effectively assisted in quickly writing an image report, thereby ensuring the quality and the efficiency of the image report, reducing labor costs and time costs required for collating the image report, further improving the practicability of the method, and facilitating market promotion and application.

Figure 8:
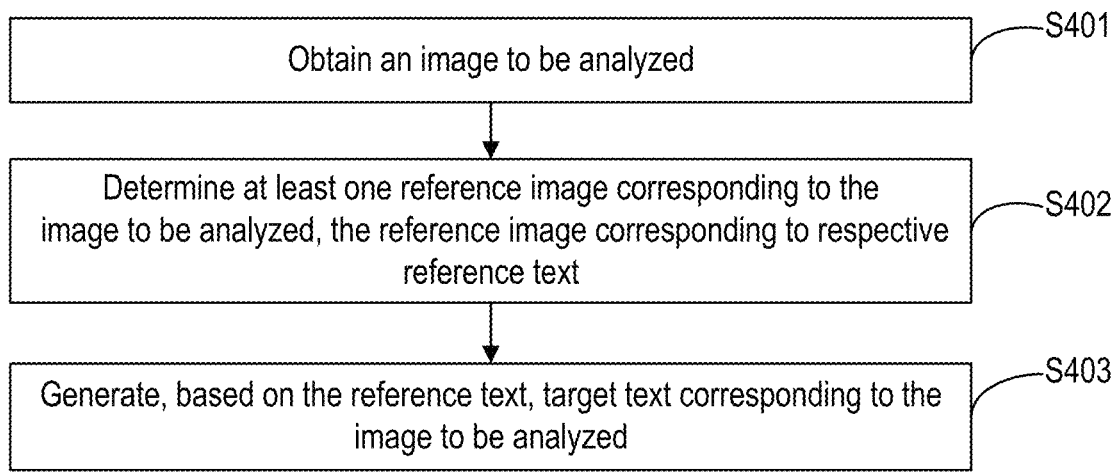
FIG. 8 is a flow diagram illustrating a method for generating text according to some embodiments of the disclosure.

FIG. 8 is a flow diagram illustrating a method for generating text according to some embodiments of the disclosure. As shown in FIG. 8, this embodiment provides a method for generating text. This generation method is executed by an apparatus for generating text. The generation apparatus may be implemented as software or a combination of software and hardware. Specifically, the method for generating text may include the following steps.

Step S401: obtain an image to be analyzed.

Step S402: determine at least one reference image corresponding to the image to be analyzed, the reference image corresponding to respective reference text.

Step S403: generate, based on the reference text, target text corresponding to the image to be analyzed.

The reference text may be text of any type used to record and store text information, and the reference text may be a sentence, a paragraph, an article, or a report. In addition, a specific implementation process and an effect of the method in this embodiment are similar to the specific implementation process and the effect of S101 through S103 in the aforementioned embodiment. For details, please refer to the description in the aforementioned embodiment; the details will not be described herein again.

It is conceivable that the method in this embodiment may also include the methods in the aforementioned embodiments shown in FIG. 2 through FIG. 6. For the parts not described in detail in this embodiment, please refer to the related description of the embodiments shown in FIG. 2 through FIG. 6. For the execution process and the technical effect of the technical solution, please refer to the description in the embodiments shown in FIG. 2 through FIG. 6, and details will not be described herein again.

In specific applications, this application embodiment provides a method for semi-automatically generating a medical image report. This method may be executed by an auxiliary apparatus for semi-automatically generating an image report. The generation apparatus executes the method for semi-automatically generating a medical image report, so as to solve the problem in which it is laborious for medical staff to write an image report after interpreting a medical image. Specifically, this method includes the following steps.

Step 1: obtain an image to be analyzed.

Figure 9:
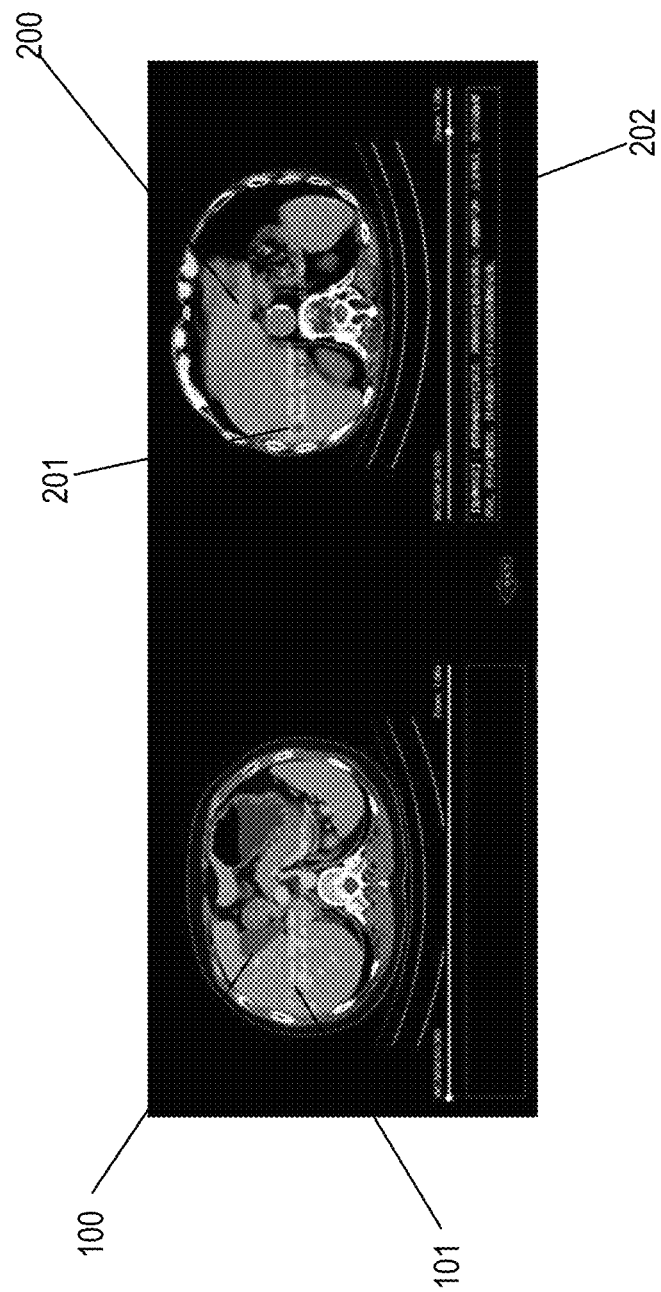
FIG. 9 illustrates the results of generating an image report according to some embodiments of the disclosure.

Specifically, an image to be analyzed captured by an imaging apparatus may be actively obtained, or an image to be analyzed directly input by the user may be obtained. The image to be analyzed may be tagged with lesion information. As shown in FIG. 9, an image on the left is an image to be analyzed 100, and an image report corresponding to the image to be analyzed 100 is in a to-be-written state. Therefore, an image report storage box at a lower portion of the image to be analyzed 100 is blank. Lesion information 101 in the image to be analyzed 100 may be tagged and displayed by means of a tagging box. It should be understood that tagging the lesion information 101 by means of the tagging box may be manually performed, or may be automatically performed by a computing device.

Step 2: obtain, by searching a historical database based on image similarity, a reference image similar to the current image and having a corresponding report.

A plurality of historical images is pre-stored in the historical database. After the image to be analyzed is obtained, similarity between the image to be analyzed and each historical image may be determined. If the similarity is greater than or equal to a pre-configured threshold, and if the historical image corresponds to an image report, then the historical image may be determined to be a reference image. As shown in FIG. 9, an image on the right is a determined reference image 200, that is, the reference image 200 retrieved by the generation apparatus involves a case similar to a case involved in the image to be analyzed 100. A lower portion of the reference image 200 corresponds to a reference image report 202, and the reference image 200 includes historical lesion information 201. The historical lesion information 201 may also be tagged and displayed by means of a tagging box.

Regarding determining a reference image, in another embodiment, a plurality of historical images is pre-stored in the historical database, and each historical image is tagged with historical lesion information and a corresponding reference image report. After lesion information of the image to be analyzed is obtained, similarity between the lesion information and each piece of historical lesion information may be determined. If the similarity is greater than or equal to a pre-configured threshold, then it is indicated that all of lesion features in the lesion information are similar to those in the historical lesion information, the lesion features including a lesion size, a lesion shape, a lesion type, a lesion position, a lesion period, etc. In this case, the historical image corresponding to the similarity may be determined to be a reference image.

It is conceivable that a reference image report corresponding to the historical image may be a pre-collated report written by a senior doctor, and therefore the accuracy thereof is ensured. In addition, as historical data in the database constantly increases, the probability of finding a similar case also increases accordingly. Therefore, if the amount of data is sufficiently large, then a reference image similar to image is necessarily found.

Step 3: generate, based on the reference image report, an image report corresponding to the image to be analyzed.

Figure 10A:
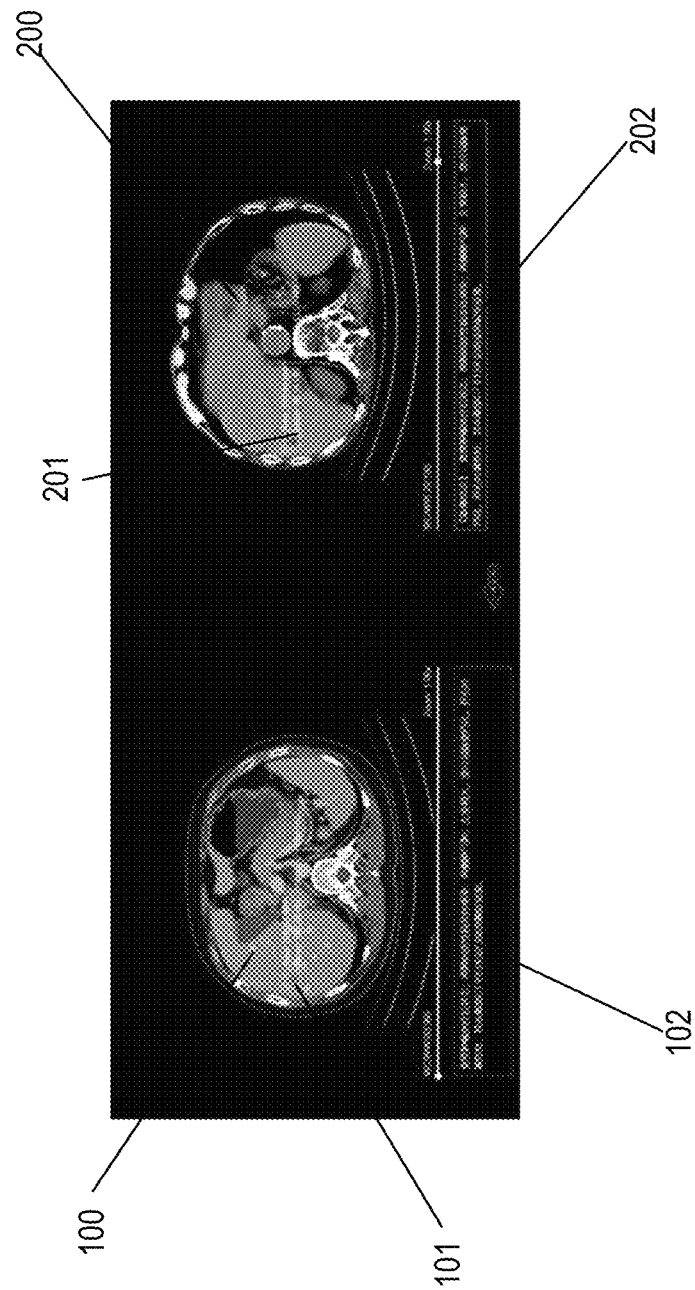
FIG. 10A illustrates the results of generating an image report according to some embodiments of the disclosure.

Specifically, as shown in FIG. 10A, in one embodiment, after the reference image report 202 corresponding to the reference image 200 is obtained, the reference image report 202 may be directly copied to a report of the current image 100 in a one-click manner, so an image report 102 corresponding to image 100 can be obtained. In this case, the content of the image report 102 is the same as the content of the reference image report 202.

After the image report 102 is obtained, it is detected whether the image report 102 corresponds to the image to be analyzed 100. If the image report 102 completely corresponds to the image to be analyzed 100, then a report generation process of the image to be analyzed 100 is directly completed. In addition, if the user is satisfied with the content of the image report 102 corresponding to the image to be analyzed 100, then the image to be analyzed 100 and the image report 102 may be stored in an associated manner, and the content may be outputted to a formal image report 102. If a slight difference exists between the image report 102 and the image to be analyzed 100, for example, if the lesion positions are different, or if the lesion sizes are different, or if the lesion periods are different, or the like, then the user may adjust the content of the image report 102, so an adjusted image report 102 corresponding to the image to be analyzed 100 can be obtained.

Figure 10B:
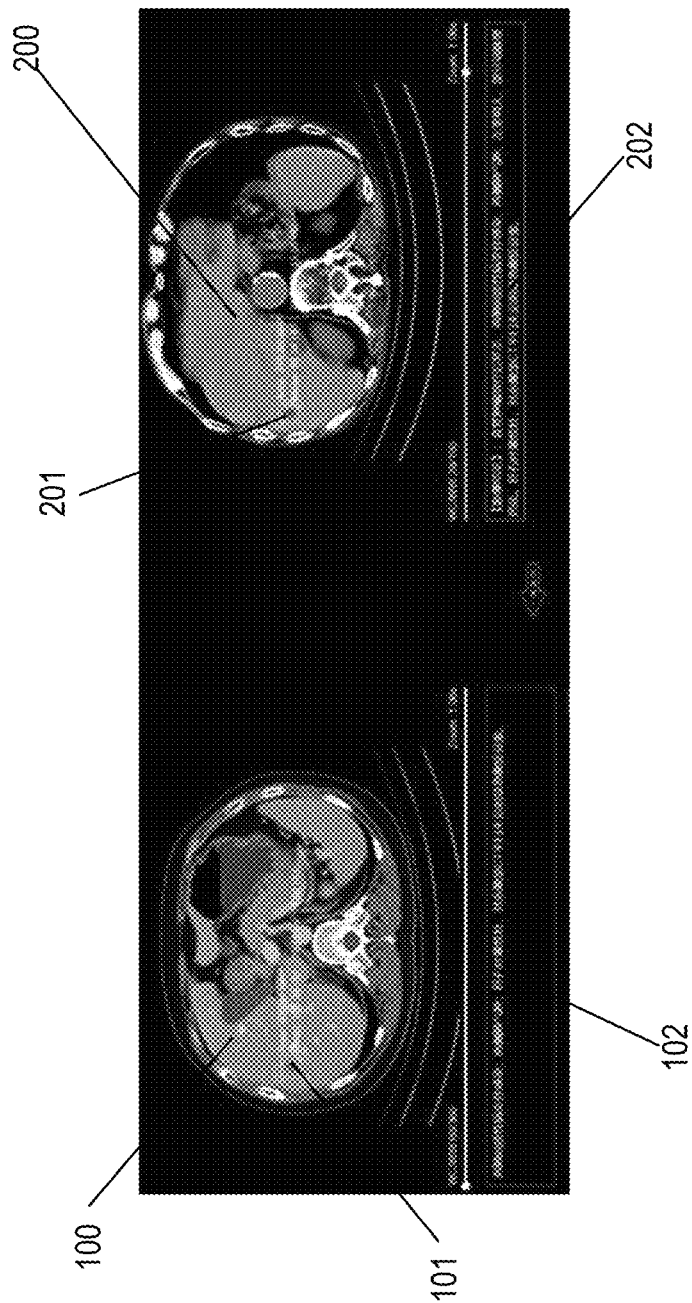
FIG. 10B illustrates the results of generating an image report according to some embodiments of the disclosure.

For example, as shown in FIG. 10B, the specific content of the obtained reference image report 202 is as follows:

manifestations after radiotherapy on an esophageal tumor include interstitial lung disease with infection, bilateral emphysema, the left ventricle being relatively large, calcification on partial coronary artery wall, and cystic lesion on the right lung lobe, and other CT plain scans on the abdomen do not indicate any obvious sign of acute abdomen.

However, the specific content of the reference image report 202 is different from that of the image to be analyzed 100. In this case, the user may adjust the content of the image report 102 obtained by copying the reference image report 202, so as to obtain an adjusted image report 102 corresponding to the image to be analyzed 100. The specific content of the adjusted image report 102 may be as follows:

manifestations after radiotherapy on an esophageal tumor include interstitial lung disease with infection, bilateral emphysema, and cystic lesion on the right lung lobe, and other CT plain scans on the abdomen do not indicate any obvious sign of acute abdomen.

Therefore, at least part of the content of the reference image report 202 is reused in the specific content of the adjusted image report 102.

Figure 14:
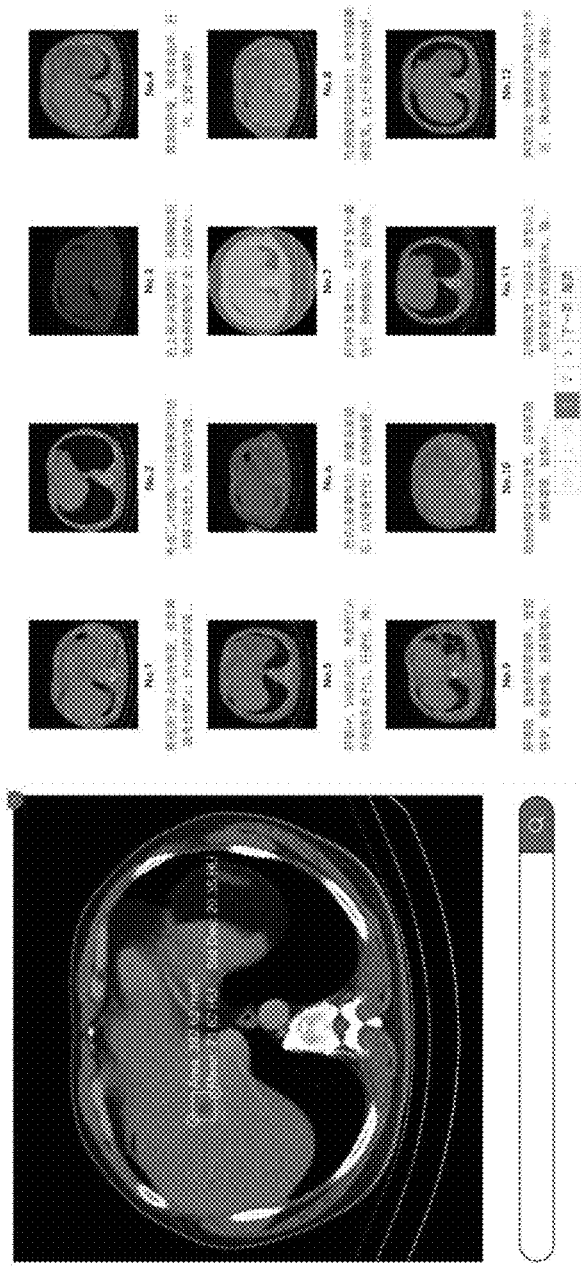
FIG. 14 illustrates the results of generating an image report according to some embodiments of the disclosure.

In another embodiment, if the user is not satisfied with the currently obtained reference image 200 corresponding to image 100, then the user may continue to review other cases in at least one retrieved reference image 200. If the number of retrieved reference images 200 is multiple, then the plurality of reference images 200 may be displayed based on a pre-configured ranking order. As shown in FIG. 14, a plurality of reference images may be displayed in descending order of similarity between the reference image and an image to be analyzed. Alternatively, the plurality of reference images may also be displayed in descending order of similarity between historical lesion information in the reference image and lesion information in the image to be analyzed.

If the number of retrieved reference images 200 is multiple, then one or a plurality of reference images 200 may be compared with the image to be analyzed 100 in sequence, and a reference image report 202 of a determined reference image 200 may be obtained by means of a one-click copy function. Alternatively, an image report 102 corresponding to image 100 may be manually inputted to an image report input box on the left.

Figure 11:
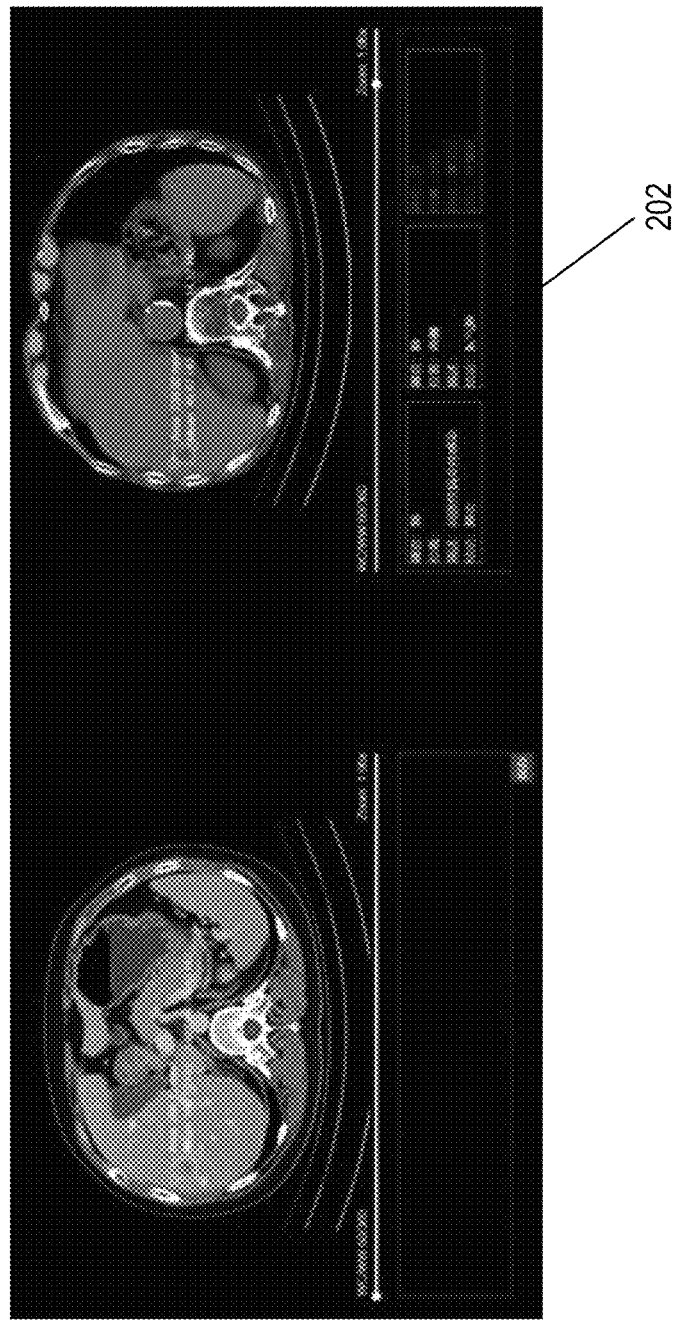
FIG. 11 illustrates the results of generating an image report according to some embodiments of the disclosure.
Figure 12:
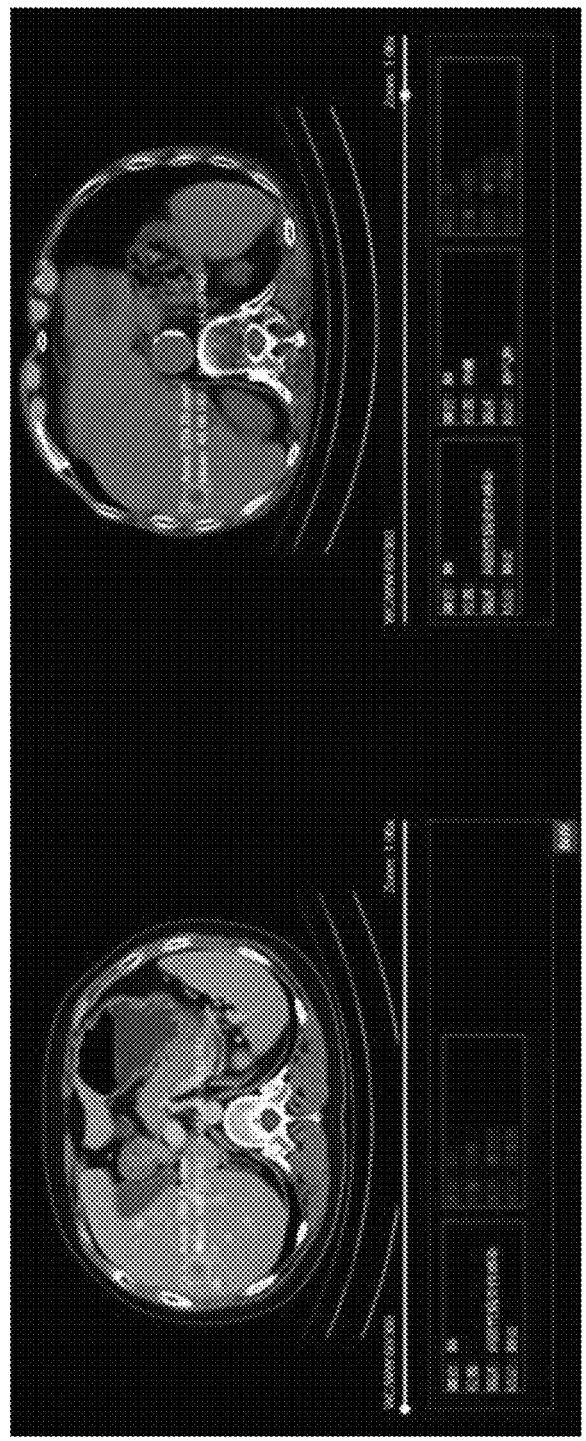
FIG. 12 illustrates the results of generating an image report according to some embodiments of the disclosure.
Figure 13:
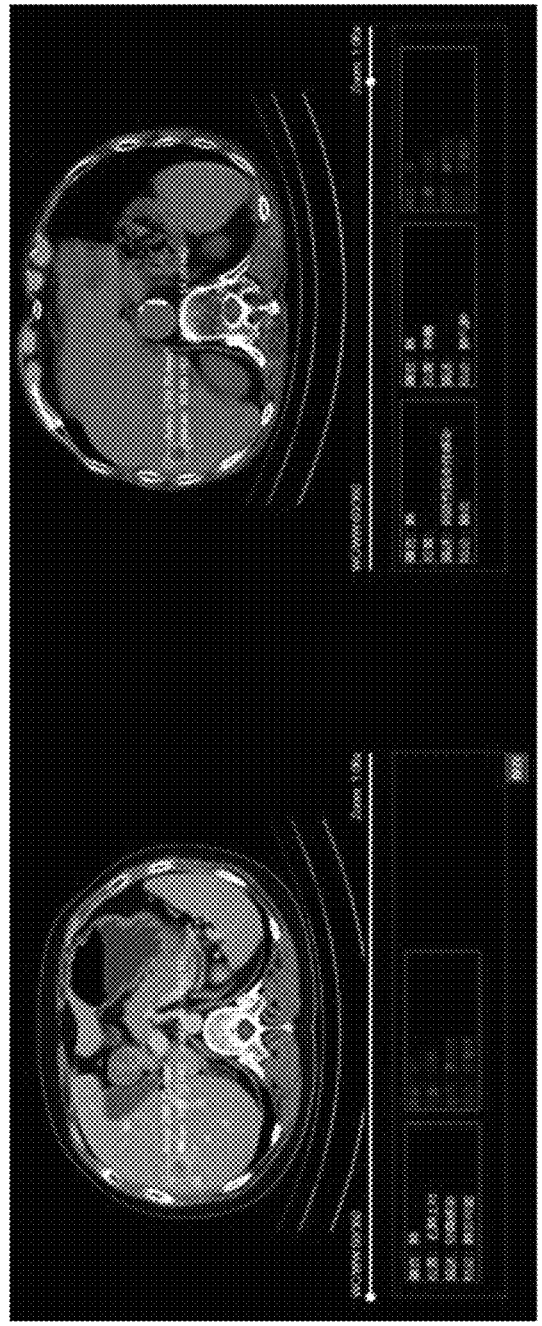
FIG. 13 illustrates the results of generating an image report according to some embodiments of the disclosure.

In addition, as shown in FIGS. 11-13, the reference image report 200 corresponding to the reference image in this embodiment may also be a structured image report. That is, the method for generating a report in this embodiment also supports drag-and-drop copy and modification functions for a structured image report. In a structured image report 202, structured reports corresponding to lesions in different parts may be presented using different colors. As shown in FIGS. 11-13, a red font is used for the liver, a yellow font is used for information about the lung organ, and a red font is used for information about the liver organ. Both the information about the lung organ and the information about the liver organ may include: a position, description information, and a conclusion. For example, for the same image, the description information of the lung organ may be interstitial disease with infection, and the conclusion for the lung organ may be pneumonia; the position of the liver organ may be the segment VI; the description of the liver organ may be a cystic lesion; the conclusion for the liver organ may be liver cyst. In addition, different background colors may be used for distinction based on whether a lesion is benign or malignant. After the structured reference image report 200 is obtained, a structured image report corresponding to the image to be analyzed may be generated based on the reference image report 200. Specifically, the content of the image report corresponding to the image to be analyzed may be firstly obtained, and after the content of the image report corresponding to the image to be analyzed is obtained, the user may review the content of the image report. If the user determines that the content of the image report is accurate, then the content of the image report may be submitted to a background, and the background generates a formatted image report based on a defined rule.

In the method for generating an image report provided by this application embodiment, a reference image similar to a current image to be analyzed and having a reference image report is found in a database by means of image retrieval; if found lesion information is also similar, then the reference image report of the reference image is copied to an image report of the current image in a one-click manner; if a slight difference exists, then the reference image report of the reference image may also be copied in a one-click manner, and then the content of the copied image report is modified; after simple collation, an image report of the current image is obtained. Therefore, medical staff are effectively assisted in quickly writing an image report, thereby ensuring the quality and the efficiency of the image report, reducing labor costs and time costs required for collating the image report, improving the practicability of the method, and facilitating market promotion and application.

Figure 15:
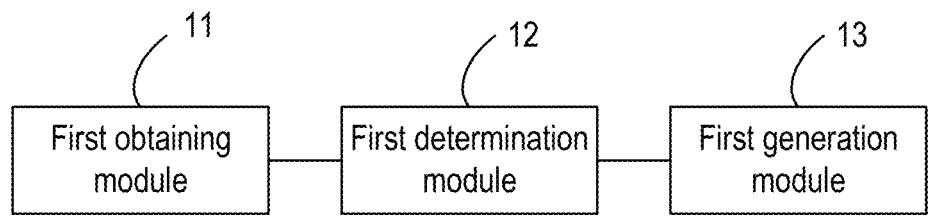
FIG. 15 is a block diagram of an apparatus for generating an image report according to some embodiments of the disclosure.

FIG. 15 is a block diagram of an apparatus for generating an image report according to some embodiments of the disclosure. As shown in FIG. 15, this embodiment provides an apparatus for generating an image report, and the generation apparatus can execute the aforementioned method for generating an image report. The apparatus may include: a first obtaining module 11, a first determination module 12, and a first generation module 13.

The first obtaining module 11 is used to obtain an image to be analyzed.

The first determination module 12 is used to determine at least one reference image corresponding to the image to be analyzed, the reference image corresponding to a respective reference image report.

The first generation module 13 is used to generate, based on the reference image report, an image report corresponding to the image to be analyzed.

Optionally, in the determining, by the first determination module 12, at least one reference image corresponding to the image to be analyzed, the first determination module 12 may be used to: obtain lesion information in the image to be analyzed; and determine, based on the lesion information, at least one reference image corresponding to the image to be analyzed.

Optionally, the lesion information includes at least one of the following: a lesion type, a lesion size, a lesion shape, a lesion position, and a lesion period.

Optionally, in the determining, by the first determination module 12 based on the lesion information, at least one reference image corresponding to the image to be analyzed, the first determination module 12 may be used to: obtain historical lesion information in at least one pre-stored historical image, where each historical image corresponds to a respective reference image report; determine similarity between the lesion information and the historical lesion information; and if the similarity is greater than or equal to a pre-configured threshold, then determine the historical image corresponding to the historical lesion information to be the at least one reference image corresponding to the image to be analyzed.

Optionally, the pre-configured threshold includes a first threshold and a second threshold, and the first threshold is greater than the second threshold. In the determining, by the first determination module 12, the historical image corresponding to the historical lesion information to be the at least one reference image corresponding to the image to be analyzed, the first determination module 12 may be used to: if the similarity is greater than or equal to the first threshold, then determine the historical image corresponding to the historical lesion information to be at least one first reference image corresponding to the image to be analyzed; and if the similarity is less than the first threshold and is greater than or equal to the second threshold, then determine the historical image corresponding to the historical lesion information to be at least one second reference image corresponding to the image to be analyzed.

Optionally, in the generating, by the first generation module 13 based on the reference image report, an image report corresponding to the image to be analyzed, the first generation module 13 may be used to: obtain a first reference image report corresponding to the first reference image; and determine the first reference image report to be an image report corresponding to the image to be analyzed.

Optionally, in the generating, by the first generation module 13 based on the reference image report, an image report corresponding to the image to be analyzed, the first generation module 13 may be used to: obtain a second reference image report corresponding to the second reference image; determine the second reference image report to be a preliminary image report corresponding to the image to be analyzed; and generate, based on the preliminary image report, a target image report corresponding to the image to be analyzed.

Optionally, in the generating, by the first generation module 13 based on the preliminary image report, a target image report corresponding to the image to be analyzed, the first generation module 13 may be used to: obtain an editing operation input by the user for the preliminary image report; and generate the target image report based on the editing operation.

Optionally, after the determining at least one reference image corresponding to the image to be analyzed, the first obtaining module 11 and the first determination module 12 in this embodiment are further used to execute the following steps: obtaining, by the first obtaining module 11, differential information between the reference image and the image to be analyzed, the differential information including a differential region and a differential degree corresponding to the differential region; and if the differential degree is greater than or equal to a pre-configured difference threshold, then distinctively displaying, by the first determination module 12, the differential region in the reference image.

Optionally, the first determination module 12 in this embodiment may be further used to: display, in descending order of the similarity, the at least one reference image and the respective reference image report corresponding to the at least one reference image.

Optionally, after the determining at least one reference image corresponding to the image to be analyzed, the first obtaining module 11 and the first determination module 12 in this embodiment are further used to execute the following steps: obtaining, by the first obtaining module 11, a keyword input by the user for the image to be analyzed; and performing, by the first determination module 12 based on the keyword, relevancy ranking on the at least one reference image.

The apparatus shown in FIG. 15 can execute the methods of the embodiments shown in FIG. 1A, FIG. 1B, FIG. 2 to FIG. 6, and FIG. 9 to FIG. 14. For the parts not described in detail in this embodiment, please refer to the related description of the embodiments shown in FIG. 1A, FIG. 1B, FIG. 2 to FIG. 6, and FIG. 9 to FIG. 14. For the execution process and the technical effect of the technical solution, please refer to the description in the embodiments shown in FIG. 1A, FIG. 1B, FIG. 2 to FIG. 6, and FIG. 9 to FIG. 14, and details will not be described herein again.

Figure 16:
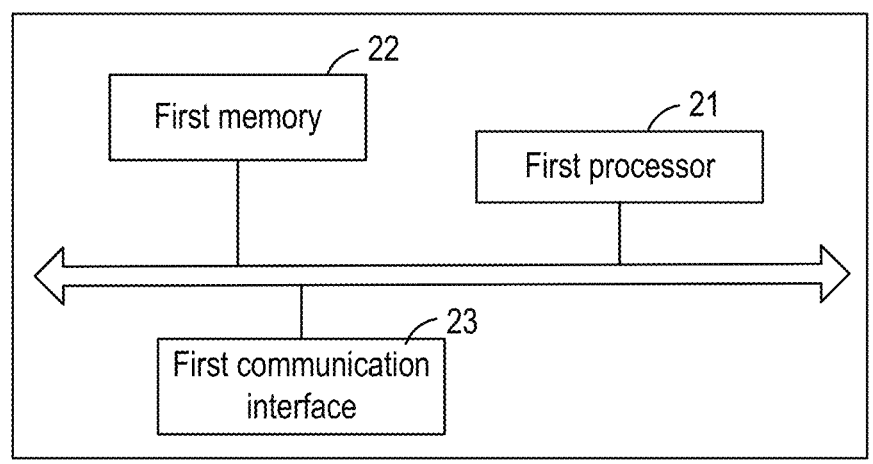
FIG. 16 is a block diagram of an electronic device corresponding to the apparatus for generating an image report according to some embodiments of the disclosure.

In a possible design, the apparatus for generating an image report shown in FIG. 15 may be implemented as an electronic device, and the electronic device may be a mobile phone, a tablet computer, a server, etc. As shown in FIG. 16, the electronic device may include a first processor 21 and a first memory 22. The first memory 22 is used to store a program enabling the electronic device to execute the methods for generating an image report provided in the embodiments shown in FIG. 1A, FIG. 1B, FIG. 2 to FIG. 6, and FIG. 9 to FIG. 14, and the first processor 21 is configured to execute the program stored in the first memory 22.

The program includes one or a plurality of computer instructions, and when executed by the first processor 21, the one or the plurality of computer instructions can implement the following steps: obtaining an image to be analyzed; determining at least one reference image corresponding to the image to be analyzed, the reference image corresponding to a respective reference image report; and generating, based on the reference image report, an image report corresponding to the image to be analyzed.

Optionally, the first processor 21 is further used to execute all of or part of the steps in the aforementioned embodiments shown in FIG. 1A, FIG. 1B, FIG. 2 to FIG. 6, and FIG. 9 to FIG. 14.

The structure of the electronic device may further include a first communication interface 23, and the first communication interface 23 is used by the electronic device to communicate with another device or a communication network.

In addition, an embodiment of the present application provides a computer storage medium, used to store computer software instructions used by an electronic device. The computer storage medium includes a program for executing the methods for generating an image report in the method embodiments shown in FIG. 1A, FIG. 1B, FIG. 2 to FIG. 6, and FIG. 9 to FIG. 14.

Figure 17:
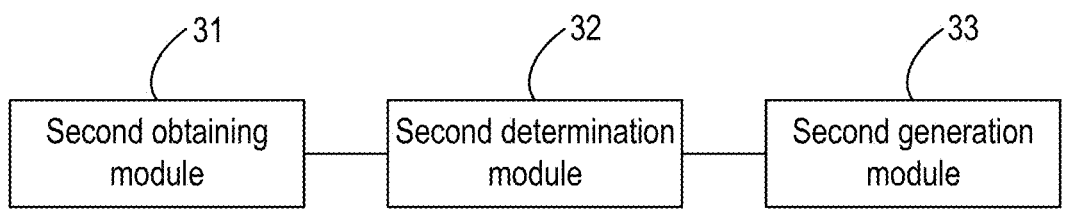
FIG. 17 is a block diagram of apparatus for generating an image report according to some embodiments of the disclosure.

FIG. 17 is a block diagram of apparatus for generating an image report according to some embodiments of the disclosure. As shown in FIG. 17, this embodiment provides apparatus for generating an image report, and the generation apparatus can execute the aforementioned method for generating an image report. The apparatus may include: a second obtaining module 31, a second determination module 32, and a second generation module 33. Specifically:

The second obtaining module 31 is used to obtain an image to be analyzed.

The second determination module 32 is used to determine at least one reference image corresponding to the image to be analyzed, the reference image corresponding to a respective reference image report.

The second obtaining module 31 is further used to obtain an execution operation input by the user for an image report control, and the image report control is used to copy the reference image report.

The second generation module 33 is used to generate, based on the execution operation, an image report corresponding to the image to be analyzed.

The apparatus shown in FIG. 17 can execute the methods of the embodiments shown in FIG. 7 and FIG. 9 to FIG. 14. For the parts not described in detail in this embodiment, please refer to the related description of the embodiments shown in FIG. 7 and FIG. 9 to FIG. 14. For the execution process and the technical effect of the technical solution, please refer to the description in the embodiments shown in FIG. 7 and FIG. 9 to FIG. 14, and details will not be described herein again.

Figure 18:
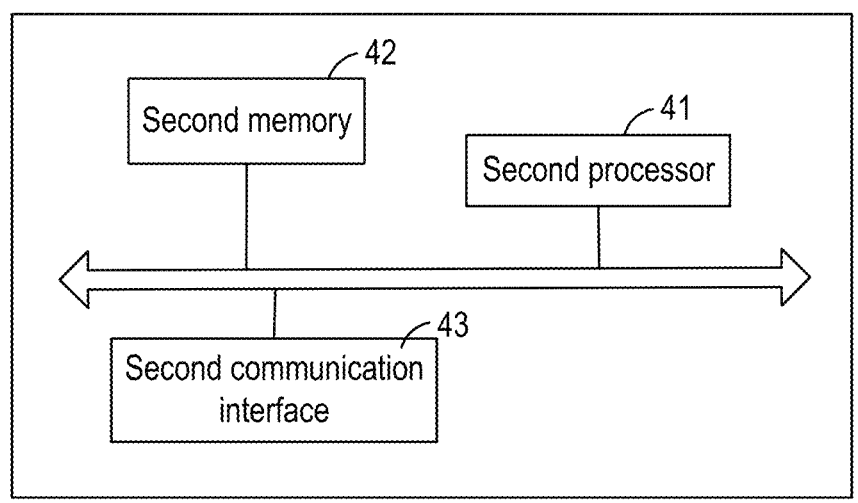
FIG. 18 is a block diagram of an electronic device corresponding to the apparatus for generating an image report according to some embodiments of the disclosure.

In a possible design, the apparatus for generating an image report shown in FIG. 17 may be implemented as an electronic device, and the electronic device may be a mobile phone, a tablet computer, a server, etc. As shown in FIG. 18, the electronic device may include a second processor 41 and a second memory 42. The second memory 42 is used to store a program enabling the electronic device to execute the methods for generating an image report provided in the embodiments shown in FIG. 7 and FIG. 9 to FIG. 14, and the second processor 41 is configured to execute the program stored in the second memory 42.

The program includes one or a plurality of computer instructions, and when executed by the second processor 41, the one or the plurality of computer instructions can implement the following steps: obtaining an image to be analyzed; determining at least one reference image corresponding to the image to be analyzed, the reference image corresponding to a respective reference image report; and obtaining an execution operation input by the user for an image report control, the image report control being used to copy the reference image report; and generating, based on the execution operation, an image report corresponding to the image to be analyzed.

The structure of the electronic device may further include a second communication interface 43, and the second communication interface 43 is used by the electronic device to communicate with another device or a communication network.

In addition, an embodiment of the present application provides a computer storage medium, used to store computer software instructions used by an electronic device. The computer storage medium includes a program for executing the methods for generating an image report in the method embodiments shown in FIG. 7 and FIG. 9 to FIG. 14.

Figure 19:
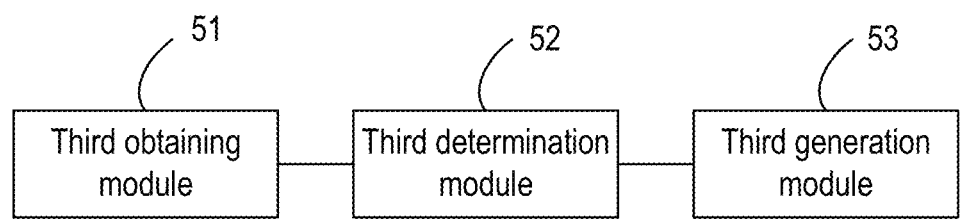
FIG. 19 is a block diagram of an apparatus for generating text according to some embodiments of the disclosure.

FIG. 19 is a block diagram of an apparatus for generating text according to some embodiments of the disclosure. As shown in FIG. 19, this embodiment provides an apparatus for generating text, and the generation apparatus can execute the aforementioned method for generating an image report. The apparatus may include: a third obtaining module 51, a third determination module 52, and a third generation module 53. Specifically:

The third obtaining module 51 is used to obtain an image to be analyzed.

The third determination module 52 is used to determine at least one reference image corresponding to the image to be analyzed, the reference image corresponding to respective reference text.

The third generation module 53 is used to generate, based on the reference text, target text corresponding to the image to be analyzed.

The apparatus shown in FIG. 19 can execute the methods of the embodiments shown in FIG. 2 to FIG. 6 and FIG. 8 to FIG. 14. For the parts not described in detail in this embodiment, please refer to the related description of the embodiments shown in FIG. 2 to FIG. 6 and FIG. 8 to FIG. 14. For the execution process and the technical effect of the technical solution, please refer to the description in the embodiments shown in FIG. 2 to FIG. 6 and FIG. 8 to FIG. 14, and details will not be described herein again.

Figure 20:
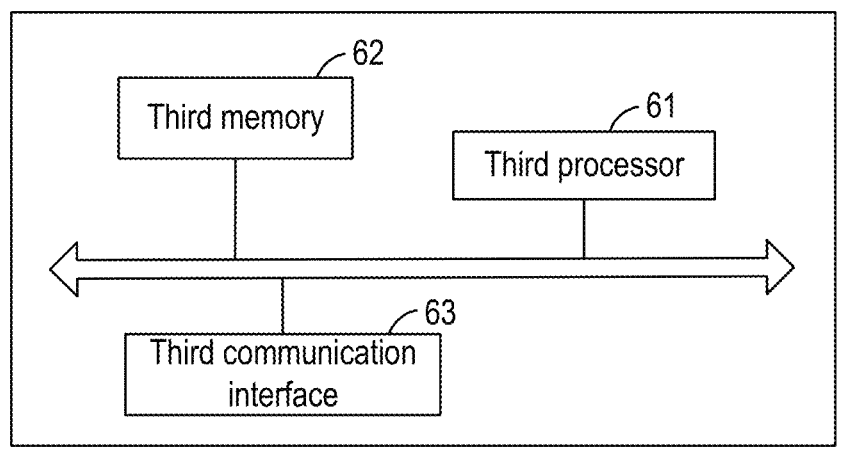
FIG. 20 is a block diagram of an electronic device corresponding to the apparatus for generating text according to some embodiments of the disclosure.

In a possible design, the apparatus for generating text shown in FIG. 19 may be implemented as an electronic device, and the electronic device may be a mobile phone, a tablet computer, a server, etc. As shown in FIG. 20, the electronic device may include a third processor 61 and a third memory 62. The third memory 62 is used to store a program enabling the electronic device to execute the methods for generating an image report provided in the embodiments shown in FIG. 2 to FIG. 6 and FIG. 8 to FIG. 14, and the third processor 61 is configured to execute the program stored in the third memory 62.

The program includes one or a plurality of computer instructions, and when executed by the third processor 61, the one or the plurality of computer instructions can implement the following steps: obtaining an image to be analyzed; determining at least one reference image corresponding to the image to be analyzed, the reference image corresponding to respective reference text; and generating, based on the reference text, target text corresponding to the image to be analyzed.

The structure of the electronic device may further include a third communication interface 63, and the third communication interface 63 is used by the electronic device to communicate with another device or a communication network.

In addition, an embodiment of the present application provides a computer storage medium, used to store computer software instructions used by an electronic device. The computer storage medium includes a program for executing the methods for generating text in the method embodiments shown in FIG. 2 to FIG. 6 and FIG. 8 to FIG. 14.

The apparatus embodiments described above are only schematic. The units described as separate components may or may not be physically separated, and the components displayed as units may or may not be physical units, that is, may be located at the same place, or may be distributed in a plurality of network units. The objective of the solution of this embodiment may be implemented by selecting a part of or all of the modules based on actual requirements. Those of ordinary skill in the art could understand and implement the present application without creative efforts.

Through the preceding description of the implementation manners, those skilled in the art can clearly understand that the implementation manners can be implemented by software plus a necessary general hardware platform, and certainly can also be implemented by a combination of hardware and software. Based on such understanding, the above technical solution essentially or the portion contributing to the prior art may be embodied in the form of a computer product. The present application may adopt the form of a computer program product implemented on one or a plurality of computer-usable storage media (including but not limited to a magnetic disk storage, a CD-ROM, an optical storage, etc.) containing computer-usable program code therein.

The present application is described with reference to flowcharts and/or block diagrams of a method, a device (system), and a computer program product according to the embodiments of the present application. It should be understood that each procedure and/or block in the flowcharts and/or block diagrams, and a combination of procedures and/or blocks in the flowcharts and/or block diagrams may be implemented with computer program instructions. These computer program instructions may be provided to a processor of a general-purpose computer, a special-purpose computer, an embedded processor, or any other programmable device to produce a machine, so instructions executed by the processor of the computer or any other programmable device generate means for implementing a specified function in one or a plurality of procedures in the flowcharts and/or one or a plurality of blocks in the block diagrams.

These computer program instructions may also be stored in a computer-readable memory that can direct a computer or any other programmable device to operate in a particular manner, so the instructions stored in the computer-readable memory produce an article of manufacture including instruction means, the instruction means implementing a specified function in one or a plurality of procedures in the flowcharts and/or one or a plurality of blocks in the block diagrams.

These computer program instructions may also be loaded onto a computer or any other programmable device, so a series of operational steps are performed on the computer or any other programmable device so as to produce computer-implemented processing, and thus the instructions executed on the computer or any other programmable device provide the steps for implementing a specified function in one or a plurality of procedures in the flowcharts and/or one or a plurality of blocks in the block diagrams.

In a typical configuration, the computing device includes one or a plurality of processors (CPUs), input/output interfaces, network interfaces, and memories.

The memory may include a computer-readable medium in the form of a non-permanent memory, a Random-Access Memory (RAM) and/or non-volatile memory or the like, such as a Read-Only Memory (ROM) or a flash memory (flash RAM). The memory is an example of the computer-readable medium.

The computer-readable medium includes permanent and non-permanent, movable and non-movable media that can achieve information storage by means of any methods or techniques. The information may be a computer-readable instruction, a data structure, a module of a program, or other data. Examples of a storage medium of a computer include, but are not limited to, a phase change memory (PRAM), a Static Random Access Memory (SRAM), a Dynamic Random Access Memory (DRAM), other types of Random Access Memories (RAMs), a Read-Only Memory (ROM), an Electrically Erasable Programmable Read-Only Memory (EEPROM), a flash memory or other memory technologies, a Compact Disk Read-Only Memory (CD-ROM), a Digital Versatile Disc (DVD) or other optical storages, a cassette tape, a magnetic tape/magnetic disk storage or other magnetic storage devices, or any other non-transmission medium, and can be used to store information accessible by a computing device. According to the definitions herein, the computer-readable medium does not include transitory computer-readable media (transitory media), such as a modulated data signal and a carrier wave.

It should be finally noted that the above embodiments are merely used for illustrating rather than limiting the technical solutions of the present application. Although the present application is described in detail with reference to the foregoing embodiments, those of ordinary skill in the art should understand that the technical solutions recorded in the foregoing embodiments may still be modified or equivalent replacement may be made on part or all of the technical features therein. These modifications or replacements will not make the essence of the corresponding technical solutions be departed from the spirit and scope of the technical solutions in the embodiments of the present application.

What is claimed is:

1. A method comprising:
  obtaining a digital image;
  retrieving a reference image from a database based on the digital image, the reference image associated with a reference image report;
  obtaining differential information between the reference image and the digital image, the differential information comprising a differential region and a differential degree corresponding to the differential region;
  when the differential degree is greater than or equal to a pre-configured difference threshold, displaying the differential region in the reference image; and
  generating an image report for the digital image based on the reference image report, the image report comprising a textual report generated at least in part on content of the reference image report.

2. The method of claim 1, further comprising:
obtaining an execution operation input by a user for an image report control, the image report control used to copy the reference image report; and
generating, based on the execution operation, the digital image report.

3. The method of claim 1, the retrieving the reference image based on the digital image comprising:
identifying lesion information in the digital image; and
retrieving the reference image based on the lesion information.

4. The method of claim 3, the lesion information comprising information selected from the group consisting of a lesion type, a lesion size, a lesion shape, a lesion position, and a lesion period.

5. The method of claim 3, the retrieving the reference image based on the lesion information comprising:
retrieving historical lesion information associated with a plurality of pre-stored historical images, each historical image in the historical images corresponding to a respective reference image report;
computing a similarity between the lesion information and the historical lesion information; and
if the similarity is greater than or equal to a pre-configured threshold, then selecting at least one historical image corresponding to the historical lesion information to be the at least one reference image.

6. The method of claim 5, wherein the pre-configured threshold comprises a first threshold and a second threshold, the first threshold is greater than the second threshold, and the selecting at least one historical image comprises:
if the similarity is greater than or equal to the first threshold, then selecting the historical image corresponding to the historical lesion information to be at least one first reference image corresponding to the digital image; and
if the similarity is less than the first threshold and is greater than or equal to the second threshold, then selecting the historical image corresponding to the historical lesion information to be at least one second reference image corresponding to the digital image.

7. The method of claim 6, the generating the digital image report comprising:
obtaining a first reference image report corresponding to the first reference image; and
using the first reference image report as the digital image report.

8. The method of claim 6, the generating the digital image report comprising:
obtaining a second reference image report corresponding to the second reference image;
identifying the second reference image report as a preliminary image report; and
generating, based on the preliminary image report, a target image report corresponding to the digital image.

9. The method of claim 8, the generating the target image report comprising:
obtaining an editing operation input by a user for the preliminary image report; and
generating the target image report based on the editing operation.

10. A non-transitory computer-readable storage medium for tangibly storing computer program instructions capable of being executed by a computer processor, the computer program instructions defining steps of:
obtaining a digital image;
retrieving a reference image from a database based on the digital image, the reference image associated with a reference image report;
obtaining differential information between the reference image and the digital image, the differential information comprising a differential region and a differential degree corresponding to the differential region;
when the differential degree is greater than or equal to a pre-configured difference threshold, displaying the differential region in the reference image; and
generating an image report for the digital image based on the reference image report, the image report comprising a textual report generated at least in part on content of the reference image report.

11. The non-transitory computer-readable storage medium of claim 10, further comprising:
obtaining an execution operation input by a user for an image report control, the image report control used to copy the reference image report; and
generating, based on the execution operation, the digital image report.

12. The non-transitory computer-readable storage medium of claim 10, the retrieving the reference image based on the digital image comprising:
identifying lesion information in the digital image; and
retrieving the reference image based on the lesion information.

13. The non-transitory computer-readable storage medium of claim 12, the retrieving the reference image based on the lesion information comprising:
retrieving historical lesion information associated with a plurality of pre-stored historical images, each historical image in the historical images corresponding to a respective reference image report;
computing a similarity between the lesion information and the historical lesion information; and
if the similarity is greater than or equal to a pre-configured threshold, then selecting at least one historical image corresponding to the historical lesion information to be the at least one reference image.

14. The non-transitory computer-readable storage medium of claim 13, wherein the pre-configured threshold comprises a first threshold and a second threshold, the first threshold is greater than the second threshold, and the selecting at least one historical image comprises:
if the similarity is greater than or equal to the first threshold, then selecting the historical image corresponding to the historical lesion information to be at least one first reference image corresponding to the digital image; and
if the similarity is less than the first threshold and is greater than or equal to the second threshold, then selecting the historical image corresponding to the historical lesion information to be at least one second reference image corresponding to the digital image.

15. An apparatus comprising:
a processor; and
a storage medium for tangibly storing thereon program logic for execution by the processor, the stored program logic comprising:
logic, executed by the processor, for obtaining a digital image;
logic, executed by the processor, for retrieving a reference image from a database based on the digital image, the reference image associated with a reference image report;

logic, executed by the processor, for obtaining differential information between the reference image and the digital image, the differential information comprising a differential region and a differential degree corresponding to the differential region;

logic, executed by the processor, for when the differential degree is greater than or equal to a pre-configured difference threshold, displaying the differential region in the reference image; and logic, executed by the processor, for generating an image report for the digital image based on the reference image report, the image report comprising a textual report generated at least in part on the content of the reference image report.

16. The apparatus of claim 15, the stored program logic further comprising:

logic, executed by the processor, for obtaining an execution operation input by a user for an image report control, the image report control used to copy the reference image report; and logic, executed by the processor, for generating, based on the execution operation, the digital image report.

17. The apparatus of claim 15, the logic for retrieving the reference image based on the digital image comprising:

logic, executed by the processor, for identifying lesion information in the digital image; and logic, executed by the processor, for retrieving the reference image based on the lesion information.

* * * * *